US012324868B2

(12) United States Patent
Roca Martinez et al.

(10) Patent No.: US 12,324,868 B2
(45) Date of Patent: Jun. 10, 2025

(54) IMPLANTS FOR SCULPTING, AUGMENTING OR CORRECTING FACIAL FEATURES SUCH AS THE CHIN

(71) Applicant: Allergan Industrie, SAS, Pringy (FR)

(72) Inventors: Jean Xavier Roca Martinez, Annecy (FR); Aurore Ayglon, Cruseilles (FR)

(73) Assignee: Allergan Industrie, SAS, Pringy (FR)

( * ) Notice: Subject to any disclaimer, the term of this patent is extended or adjusted under 35 U.S.C. 154(b) by 64 days.

(21) Appl. No.: 17/943,075

(22) Filed: Sep. 12, 2022

(65) Prior Publication Data

US 2023/0248880 A1 Aug. 10, 2023

Related U.S. Application Data

(63) Continuation of application No. 15/550,763, filed as application No. PCT/EP2016/053009 on Feb. 12, 2016, now abandoned.

(30) Foreign Application Priority Data

Feb. 13, 2015 (WO) ................. PCT/FR2015/050357
Feb. 16, 2015 (WO) ................. PCT/IB2015/000350

(51) Int. Cl.
| | | |
|---|---|---|
| A61L 27/20 | (2006.01) | |
| A61L 27/12 | (2006.01) | |
| A61L 27/52 | (2006.01) | |
| A61L 27/54 | (2006.01) | |
| A61M 5/32 | (2006.01) | |
| C08B 37/08 | (2006.01) | |

(52) U.S. Cl.
CPC ............. *A61L 27/20* (2013.01); *A61L 27/12* (2013.01); *A61L 27/52* (2013.01); *A61L 27/54* (2013.01); *A61M 5/329* (2013.01); *C08B 37/0072* (2013.01); *A61L 2300/402* (2013.01); *A61L 2400/06* (2013.01)

(58) Field of Classification Search
CPC ....... A61L 27/20; A61L 27/52; A61K 31/728; C08B 37/0072
See application file for complete search history.

(56) References Cited

U.S. PATENT DOCUMENTS

| | | | |
|---|---|---|---|
| 2,128,827 A | 8/1938 | Killian | |
| 3,548,056 A | 12/1970 | Eigen et al. | |
| 3,763,009 A | 10/1973 | Suzuki et al. | |
| 3,949,073 A | 4/1976 | Daniels et al. | |
| 4,060,081 A | 11/1977 | Yannas et al. | |
| 4,140,537 A | 2/1979 | Luck et al. | |
| 4,233,360 A | 11/1980 | Luck et al. | |
| 4,273,705 A | 6/1981 | Kato | |
| 4,279,812 A | 7/1981 | Cioca | |
| 4,424,208 A | 1/1984 | Wallace et al. | |
| 4,501,306 A | 2/1985 | Chu et al. | |
| 4,582,640 A | 4/1986 | Smestad et al. | |
| 4,582,865 A | 4/1986 | Balazs et al. | |
| 4,605,691 A | 8/1986 | Balazs et al. | |
| 4,636,524 A | 1/1987 | Balazs et al. | |
| 4,642,117 A | 2/1987 | Nguyen et al. | |
| 4,657,553 A | 4/1987 | Taylor | |
| 4,713,448 A | 12/1987 | Balazs et al. | |
| 4,716,154 A | 12/1987 | Malson et al. | |
| 4,772,419 A | 9/1988 | Malson et al. | |
| 4,803,075 A | 2/1989 | Wallace et al. | |
| 4,886,787 A | 12/1989 | de Belder et al. | |
| 4,896,787 A | 1/1990 | Delamour et al. | |
| 5,009,013 A | 4/1991 | Wiklund | |
| 5,087,446 A | 2/1992 | Suzuki et al. | |
| 5,091,171 A | 2/1992 | Yu et al. | |
| 5,143,724 A | 9/1992 | Leshchiner et al. | |
| 5,246,698 A | 9/1993 | Leshchiner et al. | |
| 5,314,874 A | 5/1994 | Miyata et al. | |
| 5,328,955 A | 7/1994 | Rhee et al. | |
| 5,356,883 A | 10/1994 | Kuo et al. | |
| 5,399,351 A | 3/1995 | Leshchiner et al. | |
| 5,428,024 A | 6/1995 | Chu et al. | |
| 5,531,716 A | 7/1996 | Luzio et al. | |
| 5,565,519 A | 10/1996 | Rhee et al. | |
| 5,571,503 A | 11/1996 | Mausner | |
| 5,614,587 A | 3/1997 | Rhee et al. | |
| 5,616,568 A | 4/1997 | Pouyani et al. | |
| 5,616,611 A | 4/1997 | Yamamoto et al. | |
| 5,616,689 A | 4/1997 | Shenoy et al. | |
| 5,633,001 A | 5/1997 | Agerup | |
| 5,643,464 A | 7/1997 | Rhee et al. | |
| 5,676,964 A | 10/1997 | Della Valle et al. | |
| 5,823,671 A | 10/1998 | Mitchell et al. | |

(Continued)

FOREIGN PATENT DOCUMENTS

| | | |
|---|---|---|
| AU | 2013202365 A1 | 5/2013 |
| CA | 949965 A | 6/1974 |
| CA | 2521961 A1 | 10/2004 |
| CA | 2805008 A1 | 1/2012 |

(Continued)

OTHER PUBLICATIONS

Adams ME. (Aug. 1993) "An Analysis of Clinical Studies of the Use of Crosslinked Hyaluronan, Hylan, in the Treatment of Osteoarthritis", The Journal of Rheumatology, 39:16-18.
Aesthetic Buyers Guide, "Juvederm Raises Standards," Jan./Feb. 2007, 5 pages, www.miinews.com.
Albano et al. (Jun. 15, 1999) "Hydroxyethyl Radicals in Ethanol Hepatotoxicity", Frontiers in Bioscience, 4:D533-D540.
Allemann et al. (2008) "Hyaluronic Acid Gel (Juvederm) Preparations in the Treatment of Facial Wrinkles and Folds", Clinical Interventions in Aging, 3(4):629-634.

(Continued)

*Primary Examiner* — Layla D Berry
(74) *Attorney, Agent, or Firm* — Mintz, Levin, Cohn, Ferris, Glovsky and Popeo, P.C.

(57) ABSTRACT

An injectable device, comprising a hyaluronic acid-based composition, useful for long lasting facial sculpting and correction of facial features, for example, for augmenting and shaping the profile, including for example, the chin, jawline or the nose, in a human being is provided. Methods of treatment are also provided.

20 Claims, 2 Drawing Sheets

(56) References Cited

U.S. PATENT DOCUMENTS

| | | |
|---|---|---|
| 5,824,333 A | 10/1998 | Scopelianos et al. |
| 5,827,529 A | 10/1998 | Ono et al. |
| 5,843,907 A | 12/1998 | Sakai et al. |
| 5,880,107 A | 3/1999 | Buenter |
| 5,886,042 A | 3/1999 | Yu et al. |
| 5,935,164 A | 8/1999 | Iversen |
| 5,972,326 A | 10/1999 | Galin et al. |
| 5,972,385 A | 10/1999 | Liu et al. |
| 5,980,930 A | 11/1999 | Fenton et al. |
| 6,013,679 A | 1/2000 | Kuo et al. |
| 6,066,325 A | 5/2000 | Wallace et al. |
| 6,129,761 A | 10/2000 | Hubbell |
| 6,224,857 B1 | 5/2001 | Romeo et al. |
| 6,335,035 B1 | 1/2002 | Drizen et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,418,934 B1 | 7/2002 | Chin |
| 6,495,148 B1 | 12/2002 | Abbiati |
| 6,521,223 B1 | 2/2003 | Calias et al. |
| 6,544,503 B1 | 4/2003 | Vanderhoff et al. |
| 6,627,620 B1 | 9/2003 | Nielsen |
| 6,630,486 B1 | 10/2003 | Royer |
| 6,685,963 B1 | 2/2004 | Taupin et al. |
| 6,716,251 B1 | 4/2004 | Asius et al. |
| 6,734,298 B1 | 5/2004 | Barbucci et al. |
| 6,767,924 B2 | 7/2004 | Yu et al. |
| 6,767,928 B1 | 7/2004 | Murphy et al. |
| 6,852,255 B2 | 2/2005 | Yang et al. |
| 6,893,466 B2 | 5/2005 | Trieu |
| 6,903,199 B2 | 6/2005 | Moon et al. |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 6,991,652 B2 | 1/2006 | Burg |
| 7,015,198 B1 | 3/2006 | Orentreich et al. |
| 7,119,062 B1 | 10/2006 | Alvis et al. |
| 7,129,209 B2 | 10/2006 | Rhee |
| 7,166,570 B2 | 1/2007 | Hunter et al. |
| 7,192,984 B2 | 3/2007 | Berg et al. |
| 7,196,180 B2 | 3/2007 | Aeschlimann et al. |
| 7,314,636 B2 | 1/2008 | Caseres et al. |
| 7,316,822 B2 | 1/2008 | Binette et al. |
| 7,491,709 B2 | 2/2009 | Carey |
| 7,741,476 B2 | 6/2010 | Lebreton |
| 7,767,452 B2 | 8/2010 | Kleinsek |
| 7,799,767 B2 | 9/2010 | Lamberti et al. |
| 7,875,296 B2 | 1/2011 | Binette et al. |
| 7,902,171 B2 | 3/2011 | Reinmuller et al. |
| 8,052,990 B2 | 11/2011 | Hermitte et al. |
| 8,053,423 B2 | 11/2011 | Lamberti et al. |
| 8,124,120 B2 | 2/2012 | Sadozai et al. |
| 8,137,702 B2 | 3/2012 | Binette et al. |
| 8,153,591 B2 | 4/2012 | Masters et al. |
| 8,288,347 B2 | 10/2012 | Collette et al. |
| 8,318,695 B2 | 11/2012 | Stroumpoulis et al. |
| 8,338,375 B2 | 12/2012 | Schroeder et al. |
| 8,338,388 B2 | 12/2012 | Lebreton |
| 8,357,795 B2 | 1/2013 | Lebreton |
| 8,394,782 B2 | 3/2013 | Stroumpoulis et al. |
| 8,394,783 B2 | 3/2013 | Stroumpoulis et al. |
| 8,394,784 B2 | 3/2013 | Stroumpoulis et al. |
| 8,455,465 B2 | 6/2013 | Gavard Molliard |
| 8,512,752 B2 | 8/2013 | Crescenzi et al. |
| 8,513,216 B2 | 8/2013 | Stroumpoulis et al. |
| 8,524,213 B2 | 9/2013 | Leshchiner et al. |
| 8,563,532 B2 | 10/2013 | Lebreton |
| 8,575,129 B2 | 11/2013 | Bellini et al. |
| 8,586,562 B2 | 11/2013 | Lebreton |
| 8,853,184 B2 | 10/2014 | Stroumpoulis et al. |
| 9,662,422 B2 | 5/2017 | Pollock et al. |
| 2001/0039336 A1 | 11/2001 | Miller et al. |
| 2002/0102311 A1 | 8/2002 | Gustavsson et al. |
| 2002/0160109 A1 | 10/2002 | Yeo et al. |
| 2003/0031638 A1 | 2/2003 | Joshi et al. |
| 2003/0093157 A1 | 5/2003 | Casares et al. |
| 2003/0119985 A1 | 6/2003 | Sehl et al. |
| 2003/0148995 A1 | 8/2003 | Piron et al. |
| 2004/0032056 A1 | 2/2004 | Vang et al. |
| 2004/0101959 A1 | 5/2004 | Marko et al. |
| 2004/0127698 A1 | 7/2004 | Tsai et al. |
| 2004/0127699 A1 | 7/2004 | Zhao et al. |
| 2004/0199241 A1 | 10/2004 | Gravett et al. |
| 2004/0265389 A1 | 12/2004 | Yui et al. |
| 2005/0013729 A1 | 1/2005 | Brown-Skrobot et al. |
| 2005/0025755 A1 | 2/2005 | Hedrick et al. |
| 2005/0101582 A1 | 5/2005 | Lyons et al. |
| 2005/0136122 A1 | 6/2005 | Sadozai et al. |
| 2005/0142152 A1 | 6/2005 | Leshchiner et al. |
| 2005/0181007 A1 | 8/2005 | Hunter et al. |
| 2005/0186261 A1 | 8/2005 | Avelar et al. |
| 2005/0186673 A1 | 8/2005 | Geistlich et al. |
| 2005/0226936 A1 | 10/2005 | Agerup |
| 2005/0271729 A1 | 12/2005 | Wang |
| 2005/0281880 A1 | 12/2005 | Wang |
| 2005/0287180 A1 | 12/2005 | Chen |
| 2006/0029578 A1 | 2/2006 | Hoemann et al. |
| 2006/0040894 A1 | 2/2006 | Hunter et al. |
| 2006/0095137 A1 | 5/2006 | Chung et al. |
| 2006/0105022 A1 | 5/2006 | Yokokawa et al. |
| 2006/0122147 A1 | 6/2006 | Wohlrab |
| 2006/0141049 A1 | 6/2006 | Lyons et al. |
| 2006/0147483 A1 | 7/2006 | Chaouk et al. |
| 2006/0189516 A1 | 8/2006 | Yang et al. |
| 2006/0194758 A1 | 8/2006 | Lebreton |
| 2006/0246137 A1 | 11/2006 | Hermitte et al. |
| 2006/0257488 A1 | 11/2006 | Hubbard |
| 2006/0286769 A1 | 12/2006 | Tsuchiya et al. |
| 2007/0026070 A1 | 2/2007 | Vonwiller et al. |
| 2007/0036745 A1 | 2/2007 | Leshchiner et al. |
| 2007/0066816 A1 | 3/2007 | Tsai et al. |
| 2007/0077292 A1 | 4/2007 | Pinsky |
| 2007/0104692 A1 | 5/2007 | Quijano et al. |
| 2007/0104693 A1 | 5/2007 | Quijano et al. |
| 2007/0203095 A1 | 8/2007 | Sadozai et al. |
| 2007/0212385 A1 | 9/2007 | David |
| 2007/0224247 A1 | 9/2007 | Chudzik et al. |
| 2007/0224278 A1 | 9/2007 | Lyons et al. |
| 2007/0298005 A1 | 12/2007 | Thibault |
| 2008/0044476 A1 | 2/2008 | Lyons et al. |
| 2008/0057091 A1 | 3/2008 | Abdellaoui et al. |
| 2008/0089918 A1 | 4/2008 | Lebreton |
| 2008/0188416 A1 | 8/2008 | Bernstein |
| 2008/0193538 A1 | 8/2008 | Kitazono et al. |
| 2008/0200430 A1 | 8/2008 | Bitterman et al. |
| 2008/0207794 A1 | 8/2008 | Wright et al. |
| 2008/0241252 A1 | 10/2008 | Lyons et al. |
| 2008/0268051 A1 | 10/2008 | Hughes et al. |
| 2008/0274946 A1 | 11/2008 | Giampapa |
| 2008/0279806 A1 | 11/2008 | Cho |
| 2008/0293637 A1 | 11/2008 | Schroeder et al. |
| 2008/0300681 A1 | 12/2008 | Rigotti et al. |
| 2009/0017091 A1 | 1/2009 | Daniloff et al. |
| 2009/0018102 A1 | 1/2009 | Moutet et al. |
| 2009/0022808 A1 | 1/2009 | Champion et al. |
| 2009/0028817 A1 | 1/2009 | Niklason et al. |
| 2009/0036403 A1 | 2/2009 | Stroumpoulis et al. |
| 2009/0042834 A1 | 2/2009 | Karageozian et al. |
| 2009/0093755 A1 | 4/2009 | Schroeder et al. |
| 2009/0098177 A1 | 4/2009 | Werkmeister et al. |
| 2009/0110671 A1 | 4/2009 | Miyata et al. |
| 2009/0110736 A1 | 4/2009 | Boutros |
| 2009/0123547 A1 | 5/2009 | Hill et al. |
| 2009/0124552 A1 | 5/2009 | Hill et al. |
| 2009/0143331 A1 | 6/2009 | Stroumpoulis et al. |
| 2009/0143348 A1 | 6/2009 | Tezel et al. |
| 2009/0148527 A1 | 6/2009 | Robinson et al. |
| 2009/0155314 A1 | 6/2009 | Tezel et al. |
| 2009/0155362 A1 | 6/2009 | Longin et al. |
| 2009/0162415 A1 | 6/2009 | Huang et al. |
| 2009/0169615 A1 | 7/2009 | Pinsky |
| 2009/0181104 A1 | 7/2009 | Rigotti et al. |
| 2009/0263447 A1 | 10/2009 | Asius et al. |

(56) References Cited

U.S. PATENT DOCUMENTS

| | | |
|---|---|---|
| 2009/0291986 A1 | 11/2009 | Pappas et al. |
| 2009/0297632 A1 | 12/2009 | Waugh |
| 2009/0317376 A1 | 12/2009 | Zukowska et al. |
| 2010/0004198 A1 | 1/2010 | Stroumpoulis et al. |
| 2010/0028437 A1 | 2/2010 | Lebreton |
| 2010/0035838 A1 | 2/2010 | Heber et al. |
| 2010/0041788 A1 | 2/2010 | Voigts et al. |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0136070 A1 | 6/2010 | Dobak et al. |
| 2010/0160948 A1 | 6/2010 | Rigotti et al. |
| 2010/0161052 A1 | 6/2010 | Rigotti et al. |
| 2010/0168780 A1 | 7/2010 | Rigotti et al. |
| 2010/0226988 A1 | 9/2010 | Lebreton |
| 2010/0247651 A1 | 9/2010 | Kestler et al. |
| 2010/0249924 A1 | 9/2010 | Powell et al. |
| 2010/0255068 A1 | 10/2010 | Stroumpoulis et al. |
| 2010/0316683 A1 | 12/2010 | Piron et al. |
| 2011/0008406 A1 | 1/2011 | Altman et al. |
| 2011/0008436 A1 | 1/2011 | Altman et al. |
| 2011/0008437 A1 | 1/2011 | Altman et al. |
| 2011/0014263 A1 | 1/2011 | Altman et al. |
| 2011/0014287 A1 | 1/2011 | Altman et al. |
| 2011/0020409 A1 | 1/2011 | Altman et al. |
| 2011/0034684 A1 | 2/2011 | Yokokawa et al. |
| 2011/0052695 A1 | 3/2011 | Jiang et al. |
| 2011/0070281 A1 | 3/2011 | Altman et al. |
| 2011/0077737 A1 | 3/2011 | Stroumpoulis et al. |
| 2011/0097381 A1 | 4/2011 | Binette et al. |
| 2011/0104800 A1 | 5/2011 | Kensy et al. |
| 2011/0111031 A1 | 5/2011 | Jiang et al. |
| 2011/0118206 A1 | 5/2011 | Lebreton |
| 2011/0150823 A1 | 6/2011 | Huang |
| 2011/0150846 A1 | 6/2011 | Van Epps |
| 2011/0171286 A1 | 7/2011 | Cecile et al. |
| 2011/0171310 A1 | 7/2011 | Gousse et al. |
| 2011/0171311 A1 | 7/2011 | Gousse et al. |
| 2011/0172180 A1 | 7/2011 | Gousse et al. |
| 2011/0183001 A1 | 7/2011 | Rosson et al. |
| 2011/0183406 A1 | 7/2011 | Kensy |
| 2011/0189292 A1 | 8/2011 | Lebreton et al. |
| 2011/0194945 A1 | 8/2011 | Kensy et al. |
| 2011/0224164 A1 | 9/2011 | Lebreton |
| 2011/0229574 A1 | 9/2011 | Guillen et al. |
| 2011/0295238 A1 | 12/2011 | Kensy et al. |
| 2012/0010146 A1 | 1/2012 | Han et al. |
| 2012/0034462 A1 | 2/2012 | Stroumpoulis et al. |
| 2012/0045420 A1 | 2/2012 | Van Epps et al. |
| 2012/0071437 A1 | 3/2012 | Stroumpoulis et al. |
| 2012/0076868 A1 | 3/2012 | Lamberti et al. |
| 2012/0095206 A1 | 4/2012 | Chen et al. |
| 2012/0100217 A1 | 4/2012 | Green et al. |
| 2012/0100611 A1 | 4/2012 | Kensy et al. |
| 2012/0156265 A1 | 6/2012 | Binette et al. |
| 2012/0164098 A1 | 6/2012 | Schroeder et al. |
| 2012/0164116 A1 | 6/2012 | Van Epps |
| 2012/0165935 A1 | 6/2012 | Van Epps |
| 2012/0171265 A1 | 7/2012 | Altman et al. |
| 2012/0172317 A1 | 7/2012 | Altman et al. |
| 2012/0172328 A1 | 7/2012 | Lebreton |
| 2012/0172985 A1 | 7/2012 | Altman et al. |
| 2012/0189589 A1 | 7/2012 | Van Epps et al. |
| 2012/0189590 A1 | 7/2012 | Van Epps et al. |
| 2012/0189699 A1 | 7/2012 | Stroumpoulis et al. |
| 2012/0189708 A1 | 7/2012 | Van Epps et al. |
| 2012/0190644 A1 | 7/2012 | D'este et al. |
| 2012/0207837 A1 | 8/2012 | Powell et al. |
| 2012/0208890 A1 | 8/2012 | Gousse et al. |
| 2012/0209381 A1 | 8/2012 | Powell et al. |
| 2012/0213852 A1 | 8/2012 | Van Epps et al. |
| 2012/0213853 A1 | 8/2012 | Van Epps et al. |
| 2012/0219627 A1 | 8/2012 | Van Epps et al. |
| 2012/0225842 A1 | 9/2012 | Cecile et al. |
| 2012/0232030 A1 | 9/2012 | Gousse et al. |
| 2012/0263686 A1 | 10/2012 | Van Epps et al. |
| 2012/0265297 A1 | 10/2012 | Altman et al. |
| 2012/0269777 A1 | 10/2012 | Van Epps et al. |
| 2012/0295870 A1 | 11/2012 | Lebreton |
| 2013/0023658 A1 | 1/2013 | Stroumpoulis et al. |
| 2013/0041038 A1 | 2/2013 | Lebreton |
| 2013/0041039 A1 | 2/2013 | Lebreton |
| 2013/0072453 A1 | 3/2013 | Gousse et al. |
| 2013/0096081 A1 | 4/2013 | Njikang et al. |
| 2013/0116188 A1 | 5/2013 | Pollock et al. |
| 2013/0116190 A1 | 5/2013 | Pollock et al. |
| 2013/0116411 A1 | 5/2013 | Pollock et al. |
| 2013/0123210 A1 | 5/2013 | Liu et al. |
| 2013/0129835 A1 | 5/2013 | Pollock et al. |
| 2013/0131011 A1 | 5/2013 | Lebreton |
| 2013/0131655 A1 | 5/2013 | Rigotti et al. |
| 2013/0136780 A1 | 5/2013 | Tezel et al. |
| 2013/0203696 A1 | 8/2013 | Njikang et al. |
| 2013/0203856 A1 | 8/2013 | Cho et al. |
| 2013/0209532 A1 | 8/2013 | Stroumpoulis et al. |
| 2013/0210760 A1 | 8/2013 | Liu et al. |
| 2013/0237615 A1 | 9/2013 | Meunier et al. |
| 2013/0244943 A1 | 9/2013 | Yu et al. |
| 2013/0244970 A1 | 9/2013 | Lebreton |
| 2013/0274222 A1 | 10/2013 | Horne et al. |
| 2013/0287758 A1 | 10/2013 | Tozzi |
| 2014/0011990 A1 | 1/2014 | Lebreton |
| 2014/0039062 A1 | 2/2014 | Stroumpoulis et al. |
| 2014/0227235 A1 | 8/2014 | Kim et al. |
| 2016/0113855 A1 | 4/2016 | Njikang et al. |
| 2017/0273886 A1 | 9/2017 | Gousse et al. |

FOREIGN PATENT DOCUMENTS

| | | |
|---|---|---|
| CN | 101502675 A | 8/2009 |
| CN | 102548590 A | 7/2012 |
| CN | 104086788 A | 10/2014 |
| EP | 0273823 A1 | 7/1988 |
| EP | 0416250 A2 | 3/1991 |
| EP | 0416846 A2 | 3/1991 |
| EP | 1247522 A1 | 10/2002 |
| EP | 1398131 A1 | 3/2004 |
| EP | 1419792 A1 | 5/2004 |
| EP | 1115433 B1 | 12/2004 |
| EP | 1532991 A1 | 5/2005 |
| EP | 1726299 A2 | 11/2006 |
| EP | 1932530 A1 | 6/2008 |
| EP | 2236523 A1 | 10/2010 |
| FR | 2733427 A1 | 10/1996 |
| FR | 2752843 A1 | 3/1998 |
| FR | 2920000 A1 | 2/2009 |
| FR | 2924615 A1 | 6/2009 |
| JP | S55-0153711 A | 11/1980 |
| JP | 2002080501 A | 3/2002 |
| JP | 2007-063177 A | 3/2007 |
| JP | 2013-544583 A | 12/2013 |
| JP | 2014-504623 A | 2/2014 |
| KR | 20110138765 A | 12/2011 |
| KR | 20130018518 A | 2/2013 |
| RU | 2477138 C1 | 3/2013 |
| WO | WO-86/00079 A1 | 1/1986 |
| WO | WO-86/000912 A1 | 2/1986 |
| WO | WO-92/000105 A1 | 1/1992 |
| WO | WO-92/20349 A1 | 11/1992 |
| WO | WO-94/001468 A1 | 1/1994 |
| WO | WO-94/002517 A1 | 2/1994 |
| WO | WO-96/33751 A1 | 10/1996 |
| WO | WO-97/004012 A1 | 2/1997 |
| WO | WO-98/035639 A1 | 8/1998 |
| WO | WO-98/035640 A1 | 8/1998 |
| WO | WO-00/001428 A1 | 1/2000 |
| WO | WO-00/08061 A1 | 2/2000 |
| WO | WO-00/46252 A1 | 8/2000 |
| WO | WO-01/079342 A2 | 10/2001 |
| WO | WO-02/005753 A1 | 1/2002 |
| WO | WO-02/006350 A1 | 1/2002 |
| WO | WO-02/009792 A1 | 2/2002 |
| WO | WO-02/017713 A1 | 3/2002 |

(56) References Cited

FOREIGN PATENT DOCUMENTS

| | | |
|---|---|---|
| WO | WO-03/007782 A2 | 1/2003 |
| WO | WO-2004/020473 A1 | 3/2004 |
| WO | WO-2004/022603 A1 | 3/2004 |
| WO | WO-2004/067575 A1 | 8/2004 |
| WO | WO-2004/073759 A1 | 9/2004 |
| WO | WO-2004/092223 A1 | 10/2004 |
| WO | WO-2005/040224 A1 | 5/2005 |
| WO | WO-2005/052035 A1 | 6/2005 |
| WO | WO-2005/067944 A1 | 7/2005 |
| WO | WO-2005/074913 A2 | 8/2005 |
| WO | WO-2005/112888 A2 | 12/2005 |
| WO | WO-2006/015490 A1 | 2/2006 |
| WO | WO-2006/021644 A1 | 3/2006 |
| WO | WO-2006/023645 A2 | 3/2006 |
| WO | WO-2006/048671 A1 | 5/2006 |
| WO | WO-2006/051950 A1 | 5/2006 |
| WO | WO-2006/056204 A1 | 6/2006 |
| WO | WO-2006/067608 A1 | 6/2006 |
| WO | WO-2007/018124 A1 | 2/2007 |
| WO | WO-2007/070617 A1 | 6/2007 |
| WO | WO-2007/077399 A2 | 7/2007 |
| WO | WO-2007/128923 A2 | 11/2007 |
| WO | WO-2007/136738 A2 | 11/2007 |
| WO | WO-2008/015249 A2 | 2/2008 |
| WO | WO-2008/034176 A1 | 3/2008 |
| WO | WO-2008/063569 A1 | 5/2008 |
| WO | WO-2008/068297 A1 | 6/2008 |
| WO | WO-2008/072230 A1 | 6/2008 |
| WO | WO-2008/077172 A2 | 7/2008 |
| WO | WO-2008/098019 A2 | 8/2008 |
| WO | WO-2008/139122 A2 | 11/2008 |
| WO | WO-2008/148071 A2 | 12/2008 |
| WO | WO-2008/148967 A2 | 12/2008 |
| WO | WO-2008/157608 A1 | 12/2008 |
| WO | WO-2009/003135 A1 | 12/2008 |
| WO | WO-2009/024350 A2 | 2/2009 |
| WO | WO-2009/024719 A1 | 2/2009 |
| WO | WO-2009/026158 A2 | 2/2009 |
| WO | WO-2009/028764 A1 | 3/2009 |
| WO | WO-2009/034559 A2 | 3/2009 |
| WO | WO-2009/073437 A1 | 6/2009 |
| WO | WO-2010/003104 A2 | 1/2010 |
| WO | WO-2010/003797 A1 | 1/2010 |
| WO | WO-2010/015900 A1 | 2/2010 |
| WO | WO-2010/026299 A1 | 3/2010 |
| WO | WO-2010/027471 A2 | 3/2010 |
| WO | WO-2010/028025 A1 | 3/2010 |
| WO | WO-2010/029344 A2 | 3/2010 |
| WO | WO-2010/038771 A1 | 4/2010 |
| WO | WO-2010/051641 A1 | 5/2010 |
| WO | WO-2010/052430 A2 | 5/2010 |
| WO | WO-2010/053918 A1 | 5/2010 |
| WO | WO-2010/061005 A1 | 6/2010 |
| WO | WO-2011/023355 A3 | 3/2011 |
| WO | WO-2011/072399 A1 | 6/2011 |
| WO | WO-2011/135150 A1 | 11/2011 |
| WO | WO-2012/008722 A2 | 1/2012 |
| WO | WO-2012/062775 A1 | 5/2012 |
| WO | WO-2012/077055 A1 | 6/2012 |
| WO | WO-2013/015579 A2 | 1/2013 |
| WO | WO-2013/036568 A1 | 3/2013 |
| WO | WO-2013/040242 A2 | 3/2013 |
| WO | WO-2013/067293 A1 | 5/2013 |
| WO | WO-2013/086024 A2 | 6/2013 |
| WO | WO-2014/055895 A1 | 4/2014 |
| WO | WO-2016/128550 A1 | 8/2016 |

OTHER PUBLICATIONS

Antunes et al. (Sep.-Oct. 2004) "Efficacy of Intrarectal Lidocaine Hydrochloride Gel for Pain Control in Patients Undergoing Transrectal Prostate Biopsy", Clinical Urology, 30(5):380-383.
Atanassoff et al. (Jun. 1997) "The Effect of Intradermal Administration of Lidocaine and Morphine on the Response to Thermal Stimulation", Department of Anesthesiology, Yale University School of Medicine, 84(6):1340-1343.
"Augment." (May 27, 2020) Merriam-Webster.com Dictionary, Merriam-Webster, https://www.merriam-webster.com/dictionary/augment, 14 pages.
Baumann et al. (Dec. 2007) "Comparison of Smooth-Gel Hyaluronic Acid Dermal Fillers With Cross-linked Bovine Collagen: a Multicenter, Double-masked, Randomized, Within-subject Study", Dermatologic Surgery, 33 (Suppl 2):S128-S135.
Beasley et al. (2009) "Hyaluronic Acid Fillers: A Comprehensive Review", Facial Plastic Surgery, 25(2):86-94.
Beer Kenneth (Oct. 2009) "Dermal Fillers and Combinations of Fillers for Facial Rejuvenation", Dermatologic Clinics, 27(4):427-432.
Belda et al. (Jun. 2005) "Hyaluronic Acid Combined with Mannitol to Improve Protection Against Free-radical Endothelial Damage: Experimental Model", Journal of Cataract & Refractive Surgery, 31(6):1213-1218.
Belmontesi et al. (Jan.-Feb. 2006) "Transdermal Injection of Restylane Subq for Aesthetic Contouring of the Cheeks, Chin, and Mandible", Aesthetic Surgery Journal, 26(1S):S28-S34.
Bircher et al. (Jun. 1996) "Delayed-type Hypersensitivity to Subcutaneous Lidocaine with Tolerance to Articaine: Confirmation by in Vivo and in Vitro Tests", Contact dermatitis, 34(6):387-389.
Bluel et al. (1981) "Evaluation of Reconstituted Collagen Tape as a Model for Chemically Modified Soft Tissues", Biomater Med Devices Artif Organs, 9(1):37-46.
Borrell et al. (Feb. 2011) "Lift capabilities of hyaluronic acid fillers", Journal of Cosmetic and Laser Therapy, 13(1):21-27.
Boulle et al., (Mar. 2009) "Lip Augmentation and Contour Correction with a Ribose Cross-linked Collagen Dermal Filler", Journal of Drugs in Dermatology, 8(3 Suppl.):1-8.
Brief Communication from EP Application No. 16706151.4, dated Feb. 7, 2022, 11 pages.
Buck et al. (Jan. 2009) "Injectable Fillers for Facial Rejuvenation: A Review", Journal of Plastic, Reconstructive & Aesthetic Surgery, 62(1):11-18.
Caffeic Acid (2018) "National Center for Biotechnology Information", PubChem Compound Database, CID=689043,https://pubchem.ncbi.nlm.nih.gov/compound/689043, 1 page.
Calderon et al. (Sep. 6, 2010) "Type II Collagen-hyaluronan Hydrogel—A Step Towards a Scaffold for Intervertebral Disc Tissue Engineering", European Cells & Materials eCM, 20:134-148.
Capozzi et al. (Aug. 1978) "Distant Migration of Silicone Gel from a Ruptured Breast Implant. Case Report", Plastic and Reconstructive Surgery, 62(2):302-303.
Carlin et al. (Jul. 1985) "Effect of Anti-inflammatory Drugs on Xanthine Oxidase and Xanthine Oxidase Induced Depolymerization of Hyaluronic Acid", Agents Actions, 16(5):377-384.
Carruthers et al. (Apr. 2009) "The Science and Art of Dermal Fillers for Soft-tissue Augmentation", Journal of Drugs in Dermatology, 8(4):335-350.
Champion et al. (Mar. 20, 2006) "Role of Target Geometry in Phagocytosis", Biophysics and Computational Biology, 103 (13) 4930-4934.
Chin et al. (Apr. 1980) "Allergic Hypersensitivity to Lidocaine Hydrochloride", International Journal of Dermatology, 19(3):147-148 (3 pages).
Chvapil et al. (Sep. 1977) "Collagen Sponge: Theory and Practice of Medical Applications", Journal of Biomedical Materials Research, 11(5):721-741.
Clark et al. (Oct. 1971) "The Influence of Triamcinolone Acetonide on Joint Stiffness in the Rat", Journal of Bone and Joint Surgery, 53(7):1409-1414.
Cohen et al. (Sep. 2003) "Organization and Adhesive Properties of the Hyaluronan Pericellular Coat of Chondrocytes and Epithelial Cells", Biophysical Journal, 85(3):1996-2005.
Cosmetic surgery and a cosmetic surgery, The Kagoshima Mitsui central clinic, Internet Archive: Wayback Machine, May 29, 2014, [Retrieved on Jan. 14, 2022], and Retrievedfrom the internet: URL:https://web.archive.org/web/20140529045521/https://chuoh-clinic-kagoshima.com/treatment/face/ago/, 8 pages.

(56) References Cited

OTHER PUBLICATIONS

Crosslinking Technical Handbook, Termo Scientific, Apr. 2009, pp. 1-48. (56 pages).
Cui et al. (2012) "The Comparison of Physicochemical Properties of Four Cross-Linked Sodium Hyaluronate Gels with Different Cross-Linking Agents", Advanced Materials Research, 396-398:1506-1512 (8 pages).
Davidenko et al. (2010) "Collagen-hyaluronic Acid Scaffolds for Adipose Tissue Engineering", Acta Biomaterialia, 8:3957-3968.
Deland et al. (Jun. 1973) "Intrathecal Toxicity Studies with Benzyl Alcohol", Toxicology and Applied Pharmacology, 25:153-156.
Desai et al. (Feb. 1995) "Molecular Weight of Heparin Using 13C Nuclear Magnetic Resonance Spectroscopy", Journal of Pharmaceutical Sciences, 84(2):212-215.
Eyre et al. (Jan. 1, 2005) "Collagen Cross-Links", Topics in Current Chemistry, 247:207-229.
Falcone et al. (Aug. 2009) "Temporary Polysaccharide Dermal Fillers: a Model for Persistence Based on Physical Properties", Dermatologic Surgery, 35(8):1238-1243.
Falcone et al. (Oct. 2008) "Crosslinked Hyaluronic Acid Dermal Fillers: a Comparison of Rheological Properties", Journal of Biomedical Materials Research Part A, 87(1):264-271.
Farley et al. (Jan.-Feb. 1994) "Diluting Lidocaine and Mepivacaine in Balanced Salt Solution Reduces", Regional Anesthesia & Pain Medicine, 19(1):48-51.
Fattahi et al. (Feb. 2008) "The Prejowl Sulcus: an Important Consideration in Lower Face Rejuvenation", Journal of Oral and Maxillofacial Surgery, 66(2):355-358.
Frati et al. (1997) "Degradation of Hyaluronic Acid by Photosensitized Riboflavin in Vitro. Modulation of the Effect by Transition Metals, Radical Quenchers, and Metal Chelators", Free Radical Biology Medicine, 22(7):1139-1144.
Fujinaga et al. (Dec. 1986) "Reproductive and Teratogenic Effects of Lidocaine in Sprague-Dawley Rats", Anesthesiology, 65(6):626-632.
Gallic Acid (2018) "National Center for Biotechnology Information", PubChem Compound Database, CID=370, https://pubchem.ncbi.nim.nih.gov/compound/370, 1 page (84 pages).
Gammaitoni et al. (Nov. 15, 2002) "Pharmacokinetics and Safety of Continuously Applied Lidocaine Patches 5%", American Journal of Health-System Pharmacy, 59(22):2215-2220.
Ginshicel Mh, Hydroxy Propyl Methyl Cellulose, Retrieved on Nov. 12, 2008 http://www.ginshicel.cn/MHPC.html, 2007, p. 1-3, 2 (3).
Gold et al., (Sep. 2007) "Use of Hyaluronic Acid Fillers for the Treatment of the Aging Face", Clinical Interventions in Aging, 2(3):369-376.
Goldberg et al. (Dec. 2009) "Breakthroughs in US Dermal Fillers for Facial Soft-Tissue Augmentation", Journal of Cosmetic and Laser Therapy, 11(4):240-247.
Gomis et al. (Jan. 2004) "Effects of Different Molecular Weight Elastoviscous Hyaluronan Solutions on Articular Nociceptive Afferents", Arthritis & Rheumatology, 50(1):314-326.
Graefe et al. (Aug. 2003) "Sensitive and Specific Photometric Determination of Mannitol in Human Serum", Clinical Chemistry and Laboratory Medicine, 41(8):1049-1055.
Grecomoro et al. (1987) "Intra-articular Treatment with Sodium Hyaluronate in Gonarthrosis: A Controlled Clinical Trial Versus Placebo", Pharmatherapeutica, 5(2):137-141.
Grillo et al. (Jan. 1962) "Thermal Reconstitution of Collagen from Solution and the Response to Its Heterologous Implantation", Journal of Surgical Research, 2:69-82.
Harding et al. (1991) "Molecular Weight Determination of Polysaccharides", Advances in Carbohydrate Analysis, 1:63-144.
Hassan et al., (May 1985) "Effects of Adjuvants to Local Anaesthetics on Their Duration. III. Experimental Studies of Hyaluronic Acid", Acta Anaesthesiologica Scandinavica, 29(4):384-388.
Hayashibara, AA2G, Sep. 23, 2007, Retrieved on Jan. 17, 2012, http://web.archive.org/web/20070923072010/http://www.hayashibara-intl.com-/cosmetics/aa2g.html, 3 pages.
Helary et al. (2010) "Concentrated Collagen Hydrogels as Dermal Substitutes", Biomaterials, 31:481-490.
Helliwell et al. (Jan. 1997) "Use of an Objective Measure of Articular Stiffness to Record Changes in Finger Joints After Intraarticular Injection of Corticosteroid", Annals of the Rheumatic Diseases, 56(1):71-73.
Hertzberger-Ten (Jan. 1991) "Intra-articular Steroids in Pauciarticular Juvenile Chronic Arthritis, Type 1", European Journal of Pediatrics, 150(3):170-172.
Hetherington et al. (Aug. 7, 2000) "Potential for Patient Harm from Intrathecal Administration of Preserved Solutions", Medical Journal of Australia, 173(3):141-143 (1 page abstract).
Hurst et al. (Jul. 1955) "Adhesive Arachnoiditis and Vascular Blockage Caused by Detergents and Other Chemical Irritants: An Experimental Study", The Journal of Pathology and Bacteriology, 70(1):167-178.
International Search Report and Written Opinion from PCT/EP2016/053009, dated May 24, 2016, 11 pages.
Intramed (Pty) Ltd, Intramed Mannitol 20% m/v Infusion, Package Insert, Jan. 1979, 2 pages.
Jones Derek (Mar. 2010) "Injectable Fillers: Principles and Practice", Wiley Blackwell, 192 Pages. (4 pages).
Jones et al. (Dec. 1995) "Intra-articular Hyaluronic Acid Compared to Intra-articular Triamcinolone Hexacetonide in Inflammatory Knee Osteoarthritis", Osteoarthritis and Cartilage, 3(4):269-273.
Juvederm Volux, Product Insert, Jul. 26, 2018, 65 pages. [Best Available Copy].
Juvederm® Vycross (Volift, Volbella, Volite) Information, www.consultingroom.com/treatment/juvederm-vycross-volift-volbella-volite (accessed Jan. 27, 2022, 7 pages.
Kablik et al. (Feb. 2009) "Comparative Physical Properties of Hyaluronic Acid Dermal Fillers", Dermatologic Surgery, 35 (Suppl. 1):302-312.
Kim et al. (Jun. 2009) "Gallotannin Isolated from *Euphorbia* Species, 1,2,6-tri-o-galloyl-beta-d-allose, Decreases Nitric Oxide Production Through Inhibition of Nuclear Factor-kappa>b and Downstream Inducible Nitric Oxide Synthase Expression in Macrophages", Biological and Pharmaceutical Bulletin, 32(6):1053-1056.
Klein et al. (Jul. 2001) "Skin filling. Collagen and other injectables of the skin", Dermatologic Clinics, 19(3):491-508.
Kopp et al. (Jun. 1985) "The Short-term Effect of Intra-articular Injections of Sodium Hyaluronate and Corticosteroid on Temporomandibular Joint Pain and Dysfunction", Journal of Oral and Maxillofacial Surgery, 43(6):429-435.
Kulicke et al. (Jul. 7, 2008) "Visco-Elastic Properties of Sodium Hyaluronate Solutions,", Institute for Technical and Macromolecular Chemistry, 1027:585-587.
Laeschke et al. (Dec. 2004) "Biocompatibility of Microparticles Into Soft Tissue Fillers", Seminars in Cutaneous Medicine and Surgery, 23(4):214-217.
Lamar et al. (Dec. 2002) "Antifibrosis Effect of Novel Gels in Anterior Ciliary Slerotomy(ACS)", The Association for Research in Vision and Ophthalmology, 43(1115):1 page.
Levy et al. (Apr. 2006) "Lidocaine Hypersensitivity After Subconjunctival Injection", Canadian Journal of Ophthalmology, 41(2):204-206.
Lindvall et al. (Jan. 1994) "Influence of Various Compounds on the Degradation of Hyaluronic Acid by a Myeloperoxidase System", Chemico-Biological Interactions, 90(1):1-12.
Lupo P Mary. (Sep. 2006) "Hyaluronic Acid Fillers in Facial Rejuvenation", Seminars in Cutaneous Medicine and Surgery, 25(3):122-126.
Mackley et al. (Mar. 2003) "Delayed-type Hypersensitivity to Lidocaine", Archives of Dermatological Research, 139(3):343-346.
Mancinelli et al. (Nov. 1997) "Intramuscular High-Dose Triamcinolone Acetonide in the Treatment of Severe Chronic Asthma", Western Journal of Medicine, 167(5): 322-329.
Matsumoto et al. (Jan. 1994) "Reducing the Discomfort of Lidocaine Administration through pH Buffering", Journal of Vascular and Interventional Radiology, 5(1):171-175.

(56) References Cited

OTHER PUBLICATIONS

McCarty et al. (Aug. 1964)"Inflammatory Reaction After Intrasynovial Injection of Microcrystalline Adrenocorticosteroid Esters", Arthritis & Rheumatology, 7:359-367.
McClelland et al. (Nov. 1997) "Evaluation of Artecoll Polymethylmethacrylate Implant for Soft-tissue Augmentation: Biocompatibility and Chemical Characterization", Plastic and Reconstructive Surgery, 100(6):1466-1474.
McPherson et al. (Jul. 1988) "Development and Biochemical Characterization of Injectable Collagen", The Journal of Dermatologic Surgery and Oncology, 14 (Suppl 1):13-20.
Millay et al. (Feb. 1991) "Vasoconstrictors in Facial Plastic Surgery", Archives of otolaryngology—head & neck surgery, 117(2):160-163.
Molliard et al. (2018) "Key Rheological Properties of Hyaluronic Acid Fillers: From Tissue Integration to Product Degradation", Plastic and Aesthetic Research, 5(17): 8 pages.
Muhn et al. (2012) "The Evolving Role of Hyaluronic Acid Fillers for Facial Volume Restoration and Contouring: a Canadian Overview", Clinical, Cosmetic and Investigational Dermatology, 5:147-158.
Nadim et al. (Dec. 2014) "Improvement of Polyphenol Properties Upon Glucosylation in a UV-induced Skin Cell Ageing Model", International Journal of Cosmetic Science, 36(6):579-587.
Notice of Opposition from EP Application No. 16706151.4, dated Sep. 3, 2020, 18 pages.
Orviský et al. (Nov. 1997) "High-molecular-weight Hyaluronan—a Valuable Tool in Testing the Antioxidative Activity of Amphiphilic Drugs Stobadine and Vinpocetine", Journal of Pharmaceutical and Biomedical Analysis, 16(3):419-424.
Osmitrol (generic name Mannitol), Official FDA Information, side effects and uses, http://www.drugs.com/pro/osmitrol.html, 2010, 10 Pages (24 pages).
Park et al. (2002) "Characterization of Porous Collagen/Hyaluronic Acid Scaffold Modified by 1- Ethyl-3-(3-Dimethylaminopropyl) Carbodiimide Cross-Linking", Biomaterials, 23(4):1205-1212.
Park et al. (Apr. 2003) "Biological Characterization of EDC-Crosslinked Collagen-Hyaluronic Acid Matrix in Dermal Tissue Restoration", Biomaterials, 24(9):1631-1641.
Park et al. (Mar. 1, 2010) "In Vitro Evaluation of Conjugated Hyaluronic Acid with Ascorbic Acid", Journal of Bone and Joint Surgery, 92-B(Suppl. 1):115-115 (1 page).
Pierre et al. (2015) "Basics of Dermal Filler Rheology", Dermatologic Surgery, 41(Suppl. 1):S120-126.
Powell F M. (1987) "Stability of Lidocaine in Aqueous Solution: Effect of Temperature, pH, Buffer, and Metal Ions on Amide Hydrolysis", Pharmaceutical Research, 4(1):42-45.
Prendergast (Oct./Nov. 2014) "Facial contouring with fillers", PFMA News, 2(1):4 pages.
Prestwich DG. (Jan. 2008) "Evaluating Drug Efficacy and Toxicology in Three Dimensions: Using Synthetic Extracellular Matrices in Drug Discovery", Accounts of Chemical Research, 41(1):139-148.
"Protrude." (May 27, 2020) Merriam-Webster.com Dictionary, Merriam-Webster, https://www.merriam-webster.com/dictionary/protrude, 12 pages.
"Protrusion." (May 26, 2020) Merriam-Webster.com Dictionary, Merriam-Webster, https://www.merriam-webster.com/dictionary/protrusion., 12 pages.
Raspaldo et al. (Sep. 2008) "Volumizing Effect of a New Hyaluronic Acid Sub-dermal Facial Filler: a Retrospective Analysis Based on 102 Cases", Journal of Cosmetic and Laser Therapy, 10(3):134-142.
Rehakova et al. (Mar. 1996) "Properties of Collagen and Hyaluronic Acid Composite Materials and Their Modification by Chemical Crosslinking", Journal of Biomedical Materials Research, 30(3):369-372.
Remington's Pharmaceutical Sciences, 1980, 16th Edition, Mack Publishing Company, Easton, Pennsylvania, 10 pages.
Romo et al. (Feb. 2005) "Chin and Prejowl Augmentation in the Management of the Aging Jawline", Facial Plastic Surgery, 21(1):38-46 (9 pages).
Rosenblatt et al. (1989) "The Effect of Collagen Fiber Size Distribution on the Release Rate of Proteins from Collagen Matrices by Diffusion", Journal of Controlled Release, 9(3):195-203.
Rosenblatt et al. (1993) "Chain Rigidity and Diffusional Release in Biopolymer Gels", Controlled Release Society, 20:264-265.
Sannino et al. (2005) "Crosslinking of Cellulose Derivatives and Hyaluronic Acid with Water-Soluble Carbodiimide", Polymer, 46(25):11206-11212.
Sculptra Product Information, Dermik Laboratories, Jun. 2004, 12 pages.
Segura et al. (Feb. 2005) "Crosslinked Hyaluronic Acid Hydrogels: A Strategy to Functionalize and Pattern", Biomaterials, 26(4):359-371.
Selvi et al. (2004) "Arthritis Induced by Corticosteroid Crystals", The Journal of Rheumatology, 31(3):622 (1 page).
Sherman et al. (May-Jun. 2009) "Avoiding dermal filler complications", Clinics in Dermatology, 27(Supplement 3):S23-S32.
Shire RJ. (Feb. 2008) "The Importance of the Prejowl Notch in Face Lifting: the Prejowl Implant", Facial Plastic Surgery Clinics of North America, 16(1):87-97.
Shu et al. (2004) "In Situ Crosslinkable Hyaluronan Hydrogels for Tissue Engineering", Biomaterials, 25(7-8): 1339-1348.
Shu et al. (2006) "Synthesis and Evaluation of Injectable, in Situ Crosslinkable Synthetic Extracellular Matrices for Tissue Engineering", Journal of Biomedical Materials Research, 79(4):902-912.
Silver et al. (1994) "Physical Properties of Hyaluronic Acid and Hydroxypropylmethylcellulose in Solution: Evaluation of Coating Ability", Journal of Applied Biomaterials, 5(1):89-98.
Skardal et al. (2010) "Bioprinting Vessel-Like Constructs Using Hyaluronan Hydrogels Crosslinked with Tetrahedral Polyethylene Glycol Tetracrylates", Biomaterials, 31(24):6173-6181.
Smith et al. (2005) "Five Percent Lidocaine Cream Applied Simultaneously to the Skin and Mucosa of the Lips Creates Excellent Anesthesia for Filler Injections", Dermatol Surgery, 31(11 Pt 2):1635-1637.
Sundaram et al. (Nov. 2010) "Comparison of the Rheological Properties of Viscosity and Elasticity in Two Categories of Soft Tissue Fillers: Calcium Hydroxylapatite and Hyaluronic Acid", Dermatologic Surgery, 36 Suppl 3(3):1859-1865 (7 pages).
Tezel et al. (2008) "The Science of Hyaluronic Acid Dermal Fillers", Journal of Cosmetic and Laser Therapy, 10(1):35-42.
Tollefson et al. (Mar.-Apr. 2007) "Computer Imaging Software for Profile Photograph Analysis", Archives of Facial Plastic Surgery, 9(2):113-119.
Tomihata et al. (1997) "Crosslinking of Hyaluronic Acid with Water-Soluable Carbodiimide", Journal of Biomedical Materials Research, 37(2):243-251.
Visiol, TRB Chemedica Ophthalmic Line, Product Info, May 2014, p. 1-2, Geneva, CH.
Visiol, Viscoelstic Gel for Use in Ocular Surgery, http://www.trbchemedica.com/index.php/option=com_content&tas, 2010, 1 Page.
Wagner L H. (1985) "The Mark-Houwink-Sakurada Equation for the Viscosity of Linear Polyethylene", Journal of Physical and Chemical Reference Data, 14(2):611-617 (8 pages).
Wahl, G. (2008) "European Evaluation of a New Hyaluronic Acid Filler Incorporating Lidocaine", Journal of Cosmetic Dermatology, 7(4):298-303.
Wang et al. (2009) "Development of Hyaluronic Acid-Based Scaffolds for Brain Tissue Engineering", Acta Biomaterialia, 5(7):2371-2384.
Waraszkiewicz et al. (1981) "Stability-Indicating High-Performance Liquid Chromatographic Analysis of Lidocaine Hydrochloride and Lidocaine Hydrochloride with Epinephrine Injectable Solutions", Journal of Pharmaceutical Sciences, 70(11):1215-1218.
Weidmann et al. (2009) "New Hyaluronic Acid Filler for Subdermal and Long-lasting Volume Restoration of the Face", European Dermatology, 65-68.
Xia et al. (2002) "Comparison of Effects of Lidocaine Hydrochloride, Buffered Lidocaine, Diphenhydramine, and Normal Saline After Intradermal Injection", Journal of Clinical Anesthesia, 14(5):339-343.

(56) References Cited

OTHER PUBLICATIONS

Yeom et al. (2010) "Effect of Cross-Linking Reagents for Hyaluronic Acid Hydrogel Dermal Fillers on Tissue Augmentation and Regeneration", Bioconjugate Chemistry, 21(2):240-247.
Yui et al. (1992) "Inflammation Responsive Degradation of Crosslinked Hyaluronic Acid Gels", Journal of Controlled Release, 26:105-116.
Yui et al. (1993) "Photo-Responsive Degradation of Heterogeneous Hydrogels Comprising Crosslinked Hyaluronic Acid and Lipid Microspheres for Temporal Drug Delivery", Journal of Controlled Release, 26(2):141-145.
Yun et al. (2004) "Hyaluronan Microspheres for Sustained Gene Delivery and Site-Specific Targeting", Biomaterials, 25(1):147-157.
Zheng et al. (2004) "In Situ Crosslinkable Hyaluronan Hydrogels for Tissue Engineering", Biomaterials, 25(7-8): 1339-1348.
Zulian et al. (Oct. 2004) "Triamcinolone Acetonide and Hexacetonide Intra-Articular Treatment of Symmetrical Joints in Juvenile Idiopathic Arthritis: A Double-Blind Trial", Rheumatology, 43(10):1288-1291.
Adelson, R.T. et al. (2008). "Objective assessment of the accuracy of computer-simulated imaging in rhinoplasty." American Journal of Otolaryngology, 29(3), 151-155.
Decision on Appeal dated Jul. 12, 2022, by the Patent Trial and Appeal Board in U.S. Appl. No. 15/550,763 (16 pages).
Decision on Appeal dated Jul. 12, 2022, by the Patent Trial and Appeal Board in U.S. Appl. No. 16/370,679 (15 pages).
EPO Decision Rejecting Opposition Against European Patent No. 3 256 179 dated Apr. 21, 2022 (15 pages).
Andre, P. (2008). "New trends in face rejuvenation by hyaluronic acid injections." Journal of Cosmetic Dermatology, 7(4), 251-258.
Carruthers, J. et al. (2010). "Volumizing with a 20-mg/ml Smooth, Highly Cohesive, Viscous Hyaluronic Acid Filler and Its Role in Facial Rejuvenation Therapy." Dermatologic Surgery : official publication for American Society for Dermatologic Surgery, Inc. 1886-1892.
Cosmetic Surgery, edited by Wu Nian, China Medical Science and Technology Press, pp. 196-199, 1st edition, 1st printing, Jun. 2014. 11 pages. [English language machine translation attached].

IMPLANTS FOR SCULPTING, AUGMENTING OR CORRECTING FACIAL FEATURES SUCH AS THE CHIN

This application is a continuation of Ser. No. 15/550,763, filed Aug. 11, 2017, which is an U.S. National Stage Application under 37 C.F.R. § 371 of International Application No. PCT/EP2016/053009, filed Feb. 12, 2016, which claims the benefit of and priority to International Application No. PCT/FR2015/050357, filed Feb. 13, 2015, and International Application No. PCT/IB2015/000350, filed Feb. 16, 2015, the entireties of each of which is incorporated herein by reference.

The present invention generally relates to injectable compositions and more specifically relates to injectable implants for adding structure and contour to the lower face.

Dermal fillers are injectable, biocompatible compositions which are well known to correct wrinkles and folds and add volume to the face. Hyaluronic acid (HA) is still considered by many to be one of the most desirable dermal fillers in that it does not pose the risk of an allergic reaction and it is temporary and reversible. The great majority of hyaluronic acid-based dermal fillers have been specifically developed for treating wrinkles and folds in skin. To be useful for facial contouring or substantial volumizing, it would be advantageous to increase the bulking effect of the compositions, also referred to as "lift". It would also be advantageous to maximize resistances of the compositions to shear and normal deformation happening in the soft tissues of the face. One of the drawbacks of maximizing these resistances, for example, elasticity and cohesivity, is that it is expected that in doing so, the viscosity of the compositions will increase to the point that they become difficult to inject with a thin needle.

There is therefore a great need for an injectable HA based implant that is specifically designed to be effective in adding substantial volume to the face, for example, for contouring the lower face, for example, for augmenting or correcting the chin, for example, for correction of chin retrusion, or for example, for augmenting or correcting the nose. It would be highly advantageous if such an implant, despite, its high viscosity, would remain easy to inject with a thin needle.

The shape of the chin has long been recognized as an important feature of the face that elicits a strong aesthetic perception that tends to be associated with personality traits of an individual. A deficient chin that lacks projection is commonly labeled a "weak chin" while prominent chins are labeled "strong chins", both implying strength of personality.

Several studies have suggested that faces with average proportions are viewed as the most attractive and that small features including a small chin are interpreted as attractive in females while the expanded chin and jaw, as a result of maturation, are interpreted as attractive in males. The appearance of the chin is a determinant of perceived attractiveness and can even influence an individual's psychosocial well-being.

Chin augmentation is conventionally performed by surgically placing a permanent implant above the jaw. The procedure is currently among the top aesthetic surgical procedures performed, based on the American Society for Aesthetic Plastic Surgery (ASAPS), and has increased 71% since 2010.

A retrusive chin can be the result of changes in growth of the lower third of the face during maturation, trauma, or facial aging, the latter of which may exacerbate the deformities or asymmetries caused by the former two. The shape of the mandible affects the mouth, chin, and neck. As an individual ages, the reduction in skeletal support of this region makes soft tissue atrophy prominent, exaggerating jowls, decreasing chin protrusion, and making the jawline look weak. Chin deformities are among the most common bony abnormalities of the face, the most common of which is horizontal microgenia characterized by the presence of normal vertical height with a retruded bony chin.

As the mandible and chin make up the framework of the lower face, augmentation methods to treat age-related chin retrusion and contour changes of the chin area or to treat microgenia have been explored for decades. Where the approach in correcting chin retrusion is to add volume, treatment methods have included chin implants, genioplasty, and injection of silicone and semi-permanent fillers, such as polymethylmethacrylate microspheres, and calcium hydroxyapatite. However, all of these treatment methods have drawbacks. For example, chin implants and genioplasty involve painful surgery that may not result in correction of chin retrusion and aesthetic blending of the area. This approach may exacerbate bone resorption and infection, resulting in the need for implant removal. Injection of semi-permanent fillers have trade-offs between volumizing capacity and adverse events associated with semi-permanent fillers.

SUMMARY OF THE INVENTION

Accordingly, an injectable implant is provided for facial sculpturing, for example, for augmenting, correcting, restoring or creating volume in the chin and other facial features in a human being.

The present invention provides temporary, reversible, HA-based structural gels manufactured specifically to provide a safe, minimally invasive method to create facial volume or facial contours. The present implants provide improved volumizing and lift properties relative to other HA-based injectables, due to a combination of mechanical properties including high elasticity and high cohesivity, while still being easily injectable with a thin needle. The present implants may be used for injection into the subcutaneous and/or supraperiosteal space. In many embodiments the implants are moldable after injection, and therefore permit sculpting, contouring, and shaping across the injected areas, for example, the chin and jaw area.

The implants generally comprise a composition comprising a hyaluronic acid (HA) crosslinked with a crosslinking agent selected from the group consisting of 1,4-butanediol diglycidyl ether (BDDE), 1,4-bis(2,3-epoxypropoxy)butane, 1,4-bisglycidyloxybutane, 1,2-bis(2,3-epoxypropoxy)ethylene and 1-(2,3-epoxypropyl)-2,3-epoxycyclohexanethe. In some embodiments, the implants generally comprise a composition comprising a hyaluronic acid (HA) crosslinked with BDDE. The compositions are suitable for injection, for example, through a fine gauge needle, and are capable of augmenting, correcting, or creating volume or lift in the face, for example, the lower face, for example, the chin or jaw, or for the midface, for example, the nose.

In some embodiments, the HA concentration is greater than 20 mg/g. In some embodiments, the HA concentration is about 21 mg/g, or about 22 mg/g, or about 23 mg/g, or about 24 mg/g, or about 25 mg/g, or about 26 mg/g, or about 27 mg/g, or about 28 mg/g, or about 29 mg/g, or about 30 mg/g or greater. In other embodiments, the composition has an HA concentration of between 22.5 mg/g to 27.5 mg/g, for example, 25.0 mg/g.

In some embodiments the method adds volume and lift to the chin or jawline or nose of the patient for a period of time in the range of about 9 months to about 24 months after the administration or injection into the chin or jawline of the patient. The composition may be moldable, for example, by physical manipulation of the tissue near the implant for a period of time after injection. The compositions may have a setting time, when the composition is no longer moldable and substantially retains its shape for the duration of the implant, within about 24 to about 48 hours after being implanted or injected.

In some embodiments, the compositions further include an anesthetic agent, for example, lidocaine HCl. For example, the compositions may include about 0.3% w/w lidocaine HCl.

In preferred embodiments, the compositions comprise a hyaluronic acid gel, preferably in an amount of about 25 mg; and lidocaine hydrochloride, preferably in an amount of about 3 mg, in a phosphate buffer (pH 7.2), preferably in a volume q.s. 1 mL.

In some embodiments, compositions are made with a mixture of low molecular weight hyaluronic acid and high molecular weight hyaluronic acid. For example, the cross-linked hyaluronic acid may be made from about 50% and about 100% of a low molecular weight hyaluronic acid prior to being crosslinked with the crosslinking agent. In some embodiments, the crosslinked hyaluronic acid is made from about 70% to about 90% of a low molecular weight hyaluronic acid prior to being crosslinked with the crosslinking agent. In some embodiments, the crosslinked hyaluronic acid is made from about 90% of a low molecular weight hyaluronic acid prior to being crosslinked with the crosslinking agent.

Using primarily a low molecular weight HA prior to crosslinking, for example about 50% or greater, for example, about 70% or about 90% low molecular weight HA, rather than using primarily a high molecular weight HA, produces a more robust, longer lasting, moldable hydrogel, having a higher cohesivity and elasticity, and more specifically suitable for facial sculpturing and augmentation by means of subcutaneous or supraperiosteal injection.

In some embodiments, the HA has a degree of crosslinking of between about 4% and about 12%. For example, the HA has a degree of crosslinking of about 4%, or about 6%, or about 8%, or about 10%. In some embodiments the HA has a degree of crosslinking of about 6.5%. In other embodiments, the HA has a degree of crosslinking of about 7.5%, or about 8.5%, or about 9.5%, or about 10.5%.

In another aspect of the invention, methods for correcting chin retrusion in a patient are provided. The methods generally comprise supraperiostally administering in the chin of the patient, an effective amount of a composition comprising BDDE-crosslinked hyaluronic acid (HA), the HA having a degree of crosslinking of about 10%, and having a HA concentration of greater than 20 mg/g. For example, in a preferred embodiment, the HA concentration is about 25 mg/g.

In a specific embodiment, the compositions comprises low molecular weight hyaluronic acid (NaHA) crosslinked with about 10% BDDE (w/w), and formulated to a concentration of about 25 mg/g with 0.3% lidocaine hydrochloride (w/w) in a phosphate buffer, pH 7.2, and supplied in a 1 mL COC (cyclic olefin copolymer) syringe.

The compositions are extrudable through a fine gauge needle, for example, a needle having a gauge of 25G, 26G, 27G, 28G, 29G or 30G. In a specific embodiment, the needle is a needle of 27 gauge×13 mm/27 G½×26 mm.

An extrusion force is the force (in Newtons N) needed to extrude the composition from its syringe at a certain rate. For example, with the supplied 1 mL COC syringe and a TSK 27G×13 mm needle, the extrusion force of some of the compositions of this invention can be between about 4N and about 15N at 13 mm/min, which is considered as very low. For example, the extrusion force can be between about 7N and about 12N, and preferably between about 8N and about 10 N.

In another aspect of the invention, methods are provide for contouring or correcting a facial feature, for example, a retruded chin, of an individual. The methods comprise, for example, the step of subdermally administering into a treatment area of the patient, an effective amount, for example, about 1.0 ml, or more, for example, about 2.0 ml or more, for example, about 3.0 ml or more, for example, 4.0 mL, of a composition of the invention. The facial feature to be improved or contoured may be a chin, for example, a retruded chin of a patient. The treatment area may include an area selected from the group consisting of the pogonion, the mentum, the left pre-jowl sulcus, the right pre-jowl sulcus, and the sublabial crease. The treatment may comprise administering the composition into two or more of the treatment areas.

Each and every feature described herein, and each and every combination of two or more of such features, is included within the scope of the present invention provided that the features included in such a combination are not mutually inconsistent.

DETAILED DESCRIPTION

Figure 1:
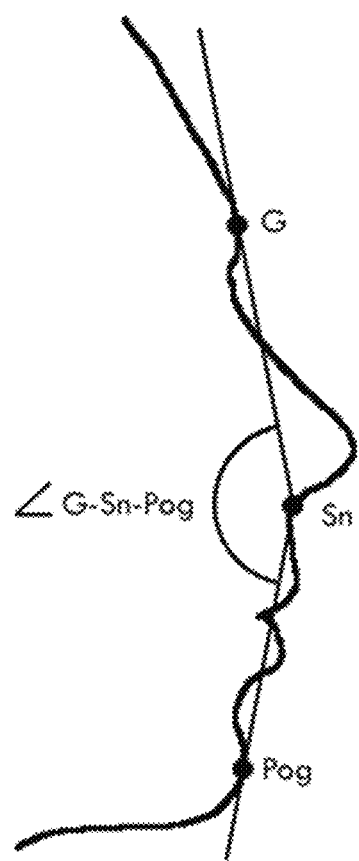
FIG. 1 shows a facial profile and landmarks for calculating G-Sn-Pog angle of a patient.

Certain terms as used in the specification are intended to refer to the following definitions, as detailed below. Where the definition of terms departs from the commonly used meaning of the term, applicant intends to utilize the definitions provided below, unless specifically indicated.

The term "about" in the context of numerical values will be readily understood by a person skilled in the art, and preferably means that specific values may be modified by +/−10%. As regards endpoints of ranges, the modifier "about" preferably means that the lower endpoint may be reduced by 10% and the upper endpoint increased by 10%. It is also contemplated that each numerical value or range disclosed in this application can be absolute, i.e. that the modifier "about" can be deleted.

All numbers herein expressing "molecular weight" of HA are to be understood as indicating the weight average molecular weight (Mw) in Daltons.

The molecular weight of HA is calculated from an intrinsic viscosity measurement using the following Mark Houwink relation:

$$\text{Intrinsic Viscosity } (L/g) = 9.78 \times 10-5 \times Mw0.690$$

The intrinsic viscosity is measured according to the procedure defined European Pharmacopoeia (HA monograph No. 1472, January/2009).

Unless stated otherwise, the molecular weight refers to the weight average molecular weight (Mw). The HA used to make the present compositions may comprise a mixture of high molecular weight HA, low molecular weight HA, and/or medium molecular weight HA, wherein the high molecular weight HA has a molecular weight greater than about 2,000,000 Da (or an intrinsic viscosity greater than 2.2 L/g) and wherein the low molecular weight HA has a molecular weight of less than about 1,000,000 Da (or an intrinsic viscosity lower than 1.4 L/g). For example, the high molecular weight HA in the present compositions may have an average molecular weight in the range about 2 MDa to about 4.0 MDa, for example, about 3.0 MDa (2.9 L/g). In another example, the high molecular weight HA may have an average molecular weight of between about 2.4 MDa to about 3.6 MDa, for example, about 3.0 MDa. The high molecular weight HA may have an intrinsic viscosity greater than about 2.2 L/g, for example, between about 2.5 L/g to about 3.3 L/g.

Low molecular weight HA can have a molecular weight of between about 200,000 Da (0.2 MDa) to less than 1.0 MDa, for example, between about 300,000 Da (0.3 MDa) to about 750,000 Da (1.1 L/g), up to but not exceeding 0.99 MDa (1.4 L/g). The low molecular weight HA may have an intrinsic viscosity of less than about 1.40 L/g, for example, between about 0.6 L/g and about 1.2 L/g.

Preferably, there is no overlap between the molecular weight distribution of the low and high molecular weight HA materials.

Preferably, the mixture of the low molecular weight HA and high molecular weight HA has a bimodal molecular weight distribution. The mixture may also have a multimodal distribution.

In one aspect of the invention, the compositions comprise HA having a high molecular weight component and a low molecular weight component, and the high molecular weight component has a weight average molecular weight at least twice the weight average molecular weight of the low molecular weight component.

"Degree of crosslinking" as used herein refers to the intermolecular junctions joining the individual HA polymer molecules, or monomer chains, into a permanent structure, or as disclosed herein the soft tissue filler composition. Moreover, degree of crosslinking for purposes of the present disclosure is further defined as the percent weight ratio of the crosslinking agent to HA-monomeric units within the crosslinked portion of the HA based composition. It is measured by the weight ratio of crosslinker to HA monomers.

"Uncrosslinked HA" as used herein refers to individual HA polymer molecules that are not crosslinked. Uncrosslinked HA generally remains water soluble. An uncrosslinked HA fraction may optionally also be included in the compositions, for example, to act as a lubricant and facilitate injection into the facial tissues. Such a composition may comprise an uncrosslinked HA fraction where the added uncrosslinked HA is present at a concentration between about 0.1 mg/g and about 3 mg/g. Preferably, the uncrosslinked HA may be present at a concentration between about 0.2 mg/g and about 1.5 mg/g.

In other embodiments, no uncrosslinked HA is present in the gels, or at least no uncrosslinked HA is added to the gels to act as a lubricant.

The compositions described herein display a high level of elasticity, expressed as a value of elastic modulus (G') measured by oscillation rheology with a strain of 0.8%, using a cone-plate system and measured over a range of frequencies. In some embodiments, the elastic modulus of the compositions measured at 5 Hz frequency are from about 500 Pa to about 900 Pa. This is considered as high elasticity in the context of HA-based dermal fillers and contributes to the lifting effect by making the implant more resistant to shear deformation.

Cohesivity refers to the capacity of the gel to stay attached to itself, for example, meaning the resistance to cutting and the ability to elongate or compress the gel without it separating into pieces. The cohesivity of the gels according to the present invention can be quantified as follows (cf. Derek Jones "Injectable Filers: Principles and Practice", Wiley, 2011, Chapter 3). A small sample of the gel (e.g. 1 mL) is placed onto the plane surface of a rheometer. The sample is placed such that it forms a little heap. A moveable upper plate is placed onto the sample so that the sample is fully covered, e.g. when looking at the plate in a direction perpendicular to the surface of the rheometer, the sample cannot be seen. In order to ensure this, one must chose a plate size that is larger than the sample size. Ideally, the center of the plate is placed over the sample. Typically, for 1 mL of gel material, a 25 mm diameter upper plate is used.

In the next step of the measurement, one then adjusts the gap between the moveable plate and the surface to 2.5 mm. While slowly and steadily moving the plate from this initial position towards a gap width of 0.9 mm within 2 min one records the force (Fn) exerted by the sample in normal direction on the plate.

Once a gap width of 0.9 mm is reached, the system is allowed to relax for 12 minutes. During this time, the measurement is continued. Five measurements are done. To normalize the forces measured, all 5 initial Fn values measured when the test starts are averaged (arithmetic mean) and this resulting average is subtracted from all other data points. The maximum force at the end on the compressive part of this test (when reaching the minimal 0.9 mm gap width between the upper plate and the plane) is called the compression force and is the characteristic value for determining the cohesivity of the gel.

Specifically, a force of 20 gmf (0.1962 N) or more indicates a cohesive material in the sense of the present invention. Gels with lower compression force values are generally not considered cohesive in the context of the present invention. The accuracy of this measurement is in the order of ±5 gmf. In the context of this invention, the injectable formulation has a high cohesivity of at least about 60 gmf, for example about 60 to about 200 gmf. For example, in a preferred embodiment, cohesivity is between about 60 and about 100 gmf, which will give to the implant a high resistance to pressure and normal forces in the soft tissues of the face.

In the context of a dermal filler, the cohesivity as defined above will contribute to the lift capacity (clinically called the volumizing/bulking effect) provided by the gel clinically, along with its elastic modulus G'. While cohesive gels can show a good volumizing effect, non-cohesive or weakly cohesive materials with a similar elastic modulus exhibits lower lift capacity due to the non-cohesive gel material spreading more than a more cohesive material when submitted to vertical compression. In the context of this invention, the compositions exhibit both high levels of elastic modulus and high levels of cohesivity, to maximize the lifting effect upon implantation.

In certain advantageous, exemplary embodiments, the present implants or fillers generally comprise a cohesive, sterile composition which is implantable subdermally or supraperiostially into the chin area, nose or jawline of the patient in need thereof, for example a patient desiring an improved facial profile or stronger chin. The composition generally comprises a crosslinked hyaluronic acid (HA)

crosslinked with 1,4-butanediol diglycidyl ether (BDDE); and the HA concentration of the composition is greater than 20 mg/g. For example, in some embodiments, the HA concentration is about 22.5 mg/g, or about 25 mg/g, or about 27.5 mg/g. The HA used for crosslinking may be made with a mixture of low molecular weight hyaluronic acid and high molecular weight hyaluronic acid. In some embodiments, the compositions have an elastic modulus between about 500 Pa and about 900 Pa at 5 Hz, and a cohesivity above about 60 gmf Advantageously, in some embodiments, the compositions exhibit an extrusion force between about 4N and about 15N, for example, between about 8N and about 10 N, at 13 mm/min using a 1 mL COC syringe and a 27G×13 mm needle.

In one aspect of the invention, injectable HA-based implants having an improved lift capacity, relative to commercial HA-based dermal fillers, are provided. The present implants are, in some instances in the present disclosure, referred alternatively as dermal fillers and subdermal fillers. The implants and fillers of the present invention are based on hyaluronic acids (HA) and pharmaceutically acceptable salts of HA, for example, sodium hyaluronate (NaHA). Methods of making these compositions, and methods of use of these compositions, are also provided.

As used herein, hyaluronic acid (HA) can refer to any of its hyaluronate salts, and includes, but is not limited to, sodium hyaluronate (NaHA), potassium hyaluronate, magnesium hyaluronate, calcium hyaluronate, and combinations thereof. Both HA and pharmaceutically acceptable salts thereof can be used in this invention.

In addition, in embodiments with anesthetics, the concentration of one or more anesthetics is in an amount effective to mitigate pain experienced upon injection of the composition. The at least one local anesthetic can be selected from the group of ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclomine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octocaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and salts thereof. In one embodiment, the at least one anesthetic agent is lidocaine, such as in the form of lidocaine HCl. The compositions described herein may have a lidocaine concentration of between about 0.1% and about 5% by weight of the composition, for example, about 0.2% to about 1.0% by weight of the composition. In one embodiment, the composition has a lidocaine concentration of about 0.3% by weight (w/w %) of the composition. The concentration of lidocaine in the compositions described herein can be therapeutically effective meaning the concentration is adequate to provide a therapeutic benefit without inflicting harm to the patient.

The present compositions may be manufactured by the steps of providing purified HA material for example, in the form of NaHA fibers; the HA material having a desired molecular weight, for example, a mixture of low molecular weight and high molecular weight HA at a desired ratio, hydrating the HA material; and crosslinking the hydrated HA material with a suitable crosslinking agent at the desired ratio to form a crosslinked HA-based gel. The gel may then be neutralized and swollen. If desired, a solution containing lidocaine, preferably an acidic salt of lidocaine chlorohydrate, may be added to form a HA/lidocaine gel. The gel may be homogenized, for example, by beating or mixing with a shear force. The homogenized composition may then be packaged in syringes. The syringes are then sterilized by autoclaving at an effective temperature and pressure. For example, the compositions are sterilized by autoclaving, for example, being exposed to temperatures of at least about 120° C. to about 130° C. and/or pressures of at least about 12 pounds per square inch (PSI) to about 20 PSI for a period of at least about 1 minute to about 15 minutes. The sterilized syringes are packaged along with a fine gauge needle for use by a physician.

More specifically, the initial raw HA material may comprise fibers or powder of NaHA, for example, bacterial-sourced NaHA fibers. Alternatively, the HA material may be animal derived, for example, from rooster combs. It is contemplated that the HA material may be a combination of raw materials including HA and at least one other polysaccharide, for example, another glycosaminoglycan (GAG).

In one method of manufacturing the compositions, pure, dry NaHA fibers are hydrated in an alkaline solution to produce an uncrosslinked NaHA gel. Any suitable alkaline solution may be used to hydrate the NaHA in this step, for example, but not limited to aqueous solutions containing sodium hydroxide (NaOH), potassium hydroxide (KOH), sodium bicarbonate ($NaHCO_3$), lithium hydroxide (LiOH), and the like. The resulting alkaline gel will have a pH above 7.5. The pH of the resulting alkaline gel can have a pH greater than 9, or a pH greater than 10, or a pH greater than 12, or a pH greater than 13.

The next step in the manufacturing process may include the step of crosslinking the hydrated, alkaline NaHA gel with a suitable crosslinking agent. The crosslinking agent may be any agent known to be suitable for crosslinking polysaccharides and their derivatives via their hydroxyl groups. One particular suitable crosslinking agent is 1,4-butanediol diglycidyl ether (BDDE).

In another embodiment, the crosslinking of the HA is accomplished during hydration of the HA fibers, by hydrating the combined high and low molecular weight fibers in an alkaline solution containing a crosslinking agent, for example, BDDE.

The degree of crosslinking in the HA component of the present compositions is at least about 4% and is up to about 12% BDDE/HA, w/w, for example, about 10%, for example, about 8%, for example, about 6%, for example, about 4%. In a specific embodiment, the degree of crosslinking is about 6.5%. In some embodiments the HA has a degree of crosslinking of about 6.5%. In other embodiments, the HA has a degree of crosslinking of about 7.5%, or about 8.5%, or about 9.5%, or about 10.5%.

The hydrated crosslinked, HA gels may be swollen to obtain the desired HA concentration. This step can be accomplished by neutralizing the crosslinked, hydrated HA gel, for example by adding an aqueous solution containing of an acid, such as HCl. The gels are then swelled in a phosphate buffered saline (PBS) solution for a sufficient time and at a low temperature.

The gels may now be purified by conventional means such as, dialysis against a phosphate buffer, or alcohol precipitation, to recover the crosslinked material, to stabilize the pH of the material and to remove any un-reacted crosslinking agent. Additional water or a slightly alkaline aqueous solution can be added to bring the concentration of the HA in the composition to a desired concentration. In some embodiments, the HA concentration of the compositions is adjusted to above 20 mg/g, for example, to about 25 mg/g. In other embodiments, the HA concentration is adjusted to yield an HA concentration of about 21 mg/g, about 22 mg/g, about 23 mg/g, about 24 mg/g, about 26 mg/g, about 27 mg/g, about 28 mg/g, about 29 mg/g, or about 30 mg/g.

In embodiments in which an anesthetic agent is to be included in the final composition, such as lidocaine, the pH of the purified crosslinked HA gels may be adjusted to cause the gel to become slightly alkaline such that the gels have a pH of greater than about 7.2, for example, about 7.5 to about 8.0. This step may be accomplished by any suitable means, for example, by adding a suitable amount of dilute NaOH, KOH, $NaHCO_3$ or LiOH, to the gels or any other alkaline molecule, solution and/or buffering composition.

An effective amount of the anesthetic, for example, lidocaine, such as lidocaine HCl, is then added to the purified crosslinked NaHA gels. For example, in some embodiments, the lidocaine HCl is provided in a powder form which is solubilized using water for injection (WFI). The gels are kept neutral with a buffer or by adjustment with diluted NaOH in order that the final HA/lidocaine composition will have a desired, substantially neutral pH. The final compositions including lidocaine may have a lidocaine concentration of between at least about 0.1% and about 5%, for example, about 2% by weight of the composition, or in another example about 0.3%.

After the addition of the lidocaine HCl, or alternatively, during the addition of the lidocaine HCl, the HA/lidocaine gels, or compositions, are homogenized to create highly homogenous HA/lidocaine gels having a desired consistency and stability. Preferably, the homogenization step comprises mixing, stirring, or beating the gels with a controlled shearing force obtaining substantially homogenous mixtures.

After homogenizing the HA composition, an amount of uncrosslinked HA solution or gel may be added to the composition to increase lubricity.

In some embodiments, no solution of uncrosslinked HA is added to the composition after homogenization.

The compositions may then be introduced into syringes and sterilized. Syringes useful according to the present description include any syringe known in the art capable of delivering viscous dermal filler compositions. The syringes generally have an internal volume of about 0.4 mL to about 3 mL, more preferably between about 0.5 mL and about 1.5 mL or between about 0.8 mL and about 2.5 mL. This internal volume is associated with an internal diameter of the syringe which plays a key role in the extrusion force needed to inject high viscosity dermal filler compositions. The internal diameters are generally about 4 mm to about 9 mm, more preferably from about 4.5 mm to about 6.5 mm or from about 4.5 mm to about 8.8 mm. Further, the extrusion force needed to deliver the HA compositions from the syringe is dependent on the needle gauge. The gauges of needles used generally include gauges between about 18G and about 40G, more preferably about 25G to about 33G, or from about 25G to about 30G. For example, in some embodiments, the compositions are packaged in a 1 mL syringe and injected using a 27 G needle.

One preferable method of sterilization of the filled syringes is by autoclave. Autoclaving can be accomplished by applying a mixture of heat, pressure and moisture to a sample in need of sterilization. Many different sterilization temperatures, pressures and cycle times can be used for this step. For example, the filled syringes may be sterilized at a temperature of at least about 120° C. to about 130° C. or greater. Moisture may or may not be utilized. The pressure applied is in some embodiments depending on the temperature used in the sterilization process. The sterilization cycle may be at least about 1 minute to about 20 minutes or more.

Another method of sterilization incorporates the use of a gaseous species which is known to kill or eliminate transmissible agents. Preferably, ethylene oxide is used as the sterilization gas and is known in the art to be useful in sterilizing medical devices and products.

A further method of sterilization incorporates the use of an irradiation source which is known in the art to kill or eliminate transmissible agents. A beam of irradiation is targeted at the syringe containing the HA composition, and the wavelength of energy kills or eliminates the unwanted transmissible agents. Preferable energy useful include, but is not limited to ultraviolet (UV) light, gamma irradiation, visible light, microwaves, or any other wavelength or band of wavelengths which kills or eliminates the unwanted transmissible agents, preferably without substantially altering of degrading the HA composition.

Preferably, the present compositions also remain stable when stored for long periods of time. For example, many of the present compositions have a shelf life of about 6 months, about 12 months, about 18 months, or about 24 months or greater, when stored at a temperature between about 2 to 25 degrees C. In a specific embodiment, the compositions are stable at a temperature of between 2 to 25 degrees C. for a period of at least 18 months. In another specific embodiment, the compositions are stable at a temperature or between 2 to 25 degrees C. for a period of at least 24 months.

The technique for injection of the present compositions may vary with regard to the angle and orientation of the bevel, and the quantity administered. In general, the present compositions are injected subcutaneously and/or supraperiosteally to increase chin projection, limiting treatment to the pogonion, the mentum (inferior aspect of the chin), pre-jowl sulci (left and right), and sublabial (mental) crease to achieve optimal correction and aesthetic chin contour. The appropriate injection volume will be determined by the investigator but is generally not to exceed a maximum total volume of about 4.0 mL for initial and top-up treatments combined. Up to about 4.0 mL total is allowed for repeat treatment. No more than about 2.0 mL is permitted to be injected into a single treatment area at any treatment session, where treatment areas are defined as the pogonion, the mentum, the pre-jowl sulci (left and right), and the sublabial (mental) crease.

Prior to injection of the present compositions, the treatment area has to be thoroughly disinfected to ensure that there is no contamination of the injectable filler with bacteria or a foreign body (e.g., make-up, talc from gloves).

Next, the 27G ½"/27 G×13 mm needle supplied should be attached to the syringe (according to Directions for Use). Prior to injecting the present compositions, the plunger rod has to be depressed until the product visibly flows out of the needle and wipe any excess on sterile gauze.

The present compositions are injected as follows: Inject the present compositions slowly, and observe the skin for signs of colour change or discolouration. Observe the subject for pain or discomfort. Inject the present compositions in a smooth and measured manner. Insert the needle being mindful of the local vascular anatomy at the injection site. Aspirate to ensure there is no blood backflow to suggest an intravascular location of the tip of the needle.

Pogonion may be injected supraperiosteally using multiple small boluses. Mentum may be injected supraperiosteally using multiple small boluses. Pre-jowl sulci (left and right) may be injected using a deep subcutaneous fanning technique. Sublabial (mental) crease may be injected using linear, retrograde or anterograde superficial subcutaneous threading.

When treatment is completed, the treated site may be gently massaged to assure that the product is evenly distributed and conforms to the contour of the surrounding tissues. If overcorrection occurs, gently massage the area between your fingers or against an underlying bone to obtain optimal results.

The present compositions are not to be injected into the blood vessels (intravascular). Introduction of hyaluronic acid into the vasculature may occlude the vessels and could cause infarction or embolization. Symptoms of vascular occlusions and embolization include pain that is disproportionate to the procedure or remote to the injection site, immediate blanching that extends beyond the injected area and that may represent vascular tributary distribution, and colour changes that reflect ischemic tissue such as a dusky or reticular appearance.

Injecting the product too superficially or in large volumes over a small area may result in visible and persistent lumps and/or discoloration.

When using a retrograde technique, inject the present compositions applying even pressure on the plunger rod while slowly pulling the needle backward. It is important that the injection be stopped just before the needle passes the subcutaneous/dermal interface to prevent material from leaking out or ending up too superficially in the skin. When using an anterograde technique, be sure the needle is in the subcutaneous tissue before the injection is started.

If the needle is blocked, do not increase the pressure on the plunger rod but stop the injection and replace the needle.

If the treated area is swollen immediately after the injection, an ice pack may be applied to the site for a short period. If subjects report inflammatory reactions which persist for more than 1 week, or any other side effect which develops, the medical practitioner should use an appropriate treatment.

In preferred embodiments, the present compositions comprise a hyaluronic acid gel, preferably in an amount of about 25 mg; and lidocaine hydrochloride, preferably in an amount of about 3 mg, in a phosphate buffer (pH 7.2), preferably in a volume q.s. 1 mL, prefilled in e.g. a 1 mL single-use syringe, wherein the hyaluronic acid gel is crosslinked with BDDE. This prefilled e.g. 1 mL single-use syringe may be contained in a kit (blister pack) along with two single use needles (e.g. 27G ½"/27 G×13 mm needles). The content of the syringe may be sterilised by moist heat. The single-use needles may be sterilised by radiation.

The present compositions are injectable implants intended for restoration and creation of facial volume, e.g. in the chin and jaw area. The presence of lidocaine is meant to reduce the subject's pain during treatment.

Example 1

Manufacture of an Injectable Implant in Accordance with an Embodiment of the Invention Predried fibers of sodium hyaluronate (NaHA) (0.9 g) having a molecular weight of about 0.9 MDa is weighed out into a first receptacle.

Predried fibers of NaHA (0.1 g) having a molecular weight of about 3.0 MDa is weighed out into a second receptacle.

The two different grades of NaHA are combined and diluted into a 1% sodium hydroxide solution and mixed for one to two hours at between 20° C. and 50° C. to obtain a substantially homogenous, alkaline HA gel.

In a separate receptacle, the chosen crosslinking agent, 1,4-butanediol diglycidyl ether (BDDE), is diluted into a 1% sodium hydroxide solution to a final concentration of 10% BDDE (wt/wt).

To the alkaline HA gel was added 10% (wt/wt) BDDE (1 g of the previously prepared BDDE solution). The resulting mixture is mechanically homogenized.

The mixture is then maintained at 50° C. for 3 to 4.5 hours.

The resulting crosslinked HA polymer is then immersed in a phosphate buffer (PB) containing hydrochloric acid to stabilize the pH.

The crosslinked HA polymer so obtained is then immersed in baths of phosphate buffer to remove unreacted crosslinking agent and HA, providing the purified hydrogel, wherein the degree of crosslinking is about 6.5%.

Optionally, dry HA material having a high molecular weight is hydrated in 1 liter of phosphate buffer to obtain an uncrosslinked HA gel. This uncrosslinked HA gel can be added to the crosslinked HA composition to represent up to 5% (w/w) of the total HA concentration.

The hydrogel obtained is then homogenized mechanically to ensure the final homogeneity, and packed into syringes which are sterilized in an autoclave.

The gel obtained is an injectable composition that can be administered subdermally or supraperiostally through a fine gauge needle (e.g. 27 Gauge). The composition is useful for restoring, contouring, or creating facial volume, for example, in the chin, jaw area, or nose of a person, as described elsewhere herein.

In one aspect of the invention, methods are provided for improving a patient's facial profile. For example, in some embodiments, methods are provided for changing a person's G-Sn-Pog facial angle, for example, for increasing a person's G-Sn-Pog facial angle. For example, in some embodiments, methods of treatment are provided for correcting chin retrusion in a patient. In some embodiments of the invention, the patient treated an initial pre-treatment G-Sn-Pog facial angle of less than about 165°. After the treatment, the patient has an increased G-Sn-Pog facial angle, that is, a facial angle greater than the initial pre-treatment facial angle. In one embodiment, the patient has a G-Sn-Pog angle of about 1690 or greater after the step of administering. The G-Sn-Pog angle may be measured using conventional equipment and calculations, for example, may be based on calculations of facial angle derived from digital images of the patient, for example, using Canfield scientific facial imaging equipment.

FIG. 1 shows facial profile and landmarks for calculating G-Sn-Pog angle of a patient, which can be used to diagnose or determine the presence and/or degree of chin retrusion, using know methods.

The methods generally comprise administering into at least one treatment area of the face of the patient, an effective amount of a composition comprising BDDE-crosslinked hyaluronic acid (HA), the HA having a degree of crosslinking of about 6.5%, or about 10%, and having a HA concentration of greater than 20 mg/g.

In some embodiments, treatment methods are provided, the methods comprising supraperiostally administering a composition, such as described herein, into at least one treatment area of the face of a patient, wherein the patient has a G-Sn-Pog facial angle of 1450 to 165°. The facial angle value may be based on calculations of facial angle derived from digital images of the patient, or using other techniques. In accordance with some embodiments, the step of administering results in the patient having an increased G-Sn-Pog angle relative to the patient's G-Sn-Pog facial angle prior to the treatment, for example, immediately prior to the administering step. In some embodiments, the patient has an increased G-Sn-Pog angle for a period of time in the range of at least about 3 months, or more preferably, for at least about 6 months, for example, for about 9 months to about 24 months, after the step of administering. For example, the patient has an increased G-Sn-Pog angle for at least about 6 months, or for at least about 9 months, or for at least about 12 months or for at least about 18 months or for at least about 24 months for after the step of administering.

In some embodiments, the treatment area is an area selected from the group consisting of the pogonion, the mentum, the left pre-jowl sulcus, the right pre-jowl sulcus, and the sublabial crease. The treatment may comprise administering the composition into two or more of the treatment areas. The administration comprises supraperiostally or subdermally injecting the compositions in an amount of between about 0.5 mL and about 3.0 mL per treatment area. In some embodiments, the amount injected into a given treatment area is no greater than 2.0 mL. In some embodiments, the total amount injected in a single treatment session, over all treatment areas, is between 2.0 mL to about 6.0 mL, for example, about 2.5 mL, about 3.0 mL, about 3.5 mL, about 4.0 mL, about 4.5 mL, about 5.0 mL, about 5.5 mL, or about 6.0 mL. In some embodiments, the amount administered into a single treatment session is about 4.0 mL or less.

Restoration and Creation of Volume in the Chin and Jaw

In one aspect, the present invention provides methods for restoring and creating volume in the chin and jaw, for example, in sculpting, shaping, and contouring across specific treatment areas of the face. The treatment areas may include one or more of the pogonion (the most projecting point on the anterior surface of the chin), mentum, (the lowest point on the chin), left and right pre-jowl sulci (left antigonion notch and right antigonion notch), and sublabial (mental) crease (the crease between the lower lip and the mentum).

Figure 2:
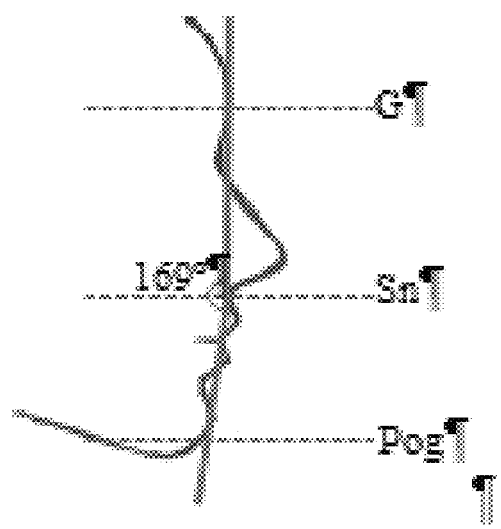
FIG. 2 shows the Burstone Angle of an average chin.

The shape and projection of the chin contribute to the proportional balance of the face that underlies attractiveness. A chin lacking projection is commonly labeled a "weak chin" whereas prominent chins are labeled "strong chins" and imply strength of personality. Several studies have suggested that faces with average proportions are viewed as the most attractive and that juvenile features including a small chin are interpreted as attractive in females while a strong chin and jaw are interpreted as attractive in males. The appearance of the chin is a determinant of perceived attractiveness and can influence an individual's psychosocial well being Average proportions are dictated by analysis of a representation of facial profiles in a population and include the distances and angles between the nose, lip, and mentum. Several soft tissue landmarks have been used in cephalometric analysis to measure and diagnose chin protrusion and retrusion deviations from average facial parameters. The intersection of the upper facial and anterior lower facial components and the angle formed by the point on the *glabella*, subnasale, and pogonion (G-Sn-Pog) has been extensively analyzed to understand the average chin projection common among populations. The Burstone angle (FIG. 2) has been defined as approximately 169° for the average chin, and the approximate angle (168° to 169°) has been confirmed in several studies.

Incrementally, deviations from the average chin result in the perception of facial unattractiveness. Analyzing the relationship between facial profile and perception of attractiveness shows that chin prominence plays a major role in this perception. To understand the relationship between the degree of chin prominence and attractiveness, a series of profile images altered in 2-mm increments from an idealized profile image was presented to a group of pretreatment orthognathic patients, clinicians, and laypeople. Subjects were asked to rate each image on a 7-point Likert scale ranging from extremely unattractive to extremely attractive. Ratings of perceived attractiveness decreased an average of 0.15 on the Likert Scale for each 2 mm of chin retrusion and were apparent after 4 mm of change. The degree of chin retrusion at which surgery was desired was 11 mm for patients and clinicians and 10 mm for laypeople. The most attractive image was that which displayed an ideal orthognathic profile with the soft tissue pogonion resting on the true vertical line.

Example 2

Method for Increasing the G Sn Pog Facial Angle in a Subject Having Chin Retrusion or a Weak Chin A composition of the invention is administered as an injectable implant, by subdermal or supraperiosteal injection in the chin and/or jaw area of a 32 year old male subject. The subject complains he has a "weak chin". The doctor measures the subject's facial angle and determines that the a G-Sn-Pog angle of about 150°, which is substantially lower than the classic Burstone angle of the average chin (approximately 169°). The measurement is based on calculations of facial angle derived from digital images obtained using Canfield imaging equipment and software.

The doctor considers the subject's chin/jaw retrusion to be amenable to correction with a treatment goal consistent with increasing chin projection horizontally (in the profile view), not chin lengthening or widening.

The doctor believes that he can provide the subject with a more attractive facial profile and a stronger jawline by using the implantable compositions described herein.

The subject undergoes three treatment sessions, including initial treatment, top-up treatment, and repeat treatment, as described below.

For each treatment, the treatment areas include at least one or more of the following treatment areas: the pogonion (the most projecting point on the anterior surface of the chin), the mentum (the lowest point on the chin), the left pre-jowl sulcus (left antigonion notch), the right pre-jowl sulcus (right antigonion notch), and/or the sublabial crease (the crease between the lower lip and the mentum).

The doctor implants no more than 2.0 mL into a single treatment area at any of the treatment sessions.

The initial treatment is performed on the subject as follows. The doctor uses aseptic skin preparation and administers anesthesia following his standard practice. The application of ice and topical anesthesia may reduce injection discomfort. Injectable anesthesia is limited to the treatment areas only is and administered with certainty not to distort the planned treatment areas.

Using needles (27 gauge×13 mm/27G ½") supplied with a kit, the doctor injects the compositions described herein subcutaneously and/or supraperiosteally to increase chin projection (horizontally in the profile view), as well as to aesthetically sculpt, contour, and shape, limiting treatment to the pogonion, mentum, pre-jowl sulci, and sublabial (mental) crease. Suitable injection techniques have been described above. The treatment goal is to increase chin projection (horizontally in the profile view) and achieve aesthetic chin contour. The doctor determines the appropriate injection volume up to about 4.0 mL for initial and possible top-up treatments combined.

The doctor gently molds the treated area using manual manipulation of the overlying tissue to achieve the desired facial contour.

A top-up treatment occurs approximately 30 days after the initial treatment if desired by the subject, or if in the doctor's opinion, optimal (full) increase in chin projection and/or aesthetic contouring was not achieved by the initial treatment. If a top-up treatment is performed, the volume of the administered composition as a combined total (initial treatment and top-up treatment) is between about 2.0 mL to about 4.0 mL.). During this visit, the doctor evaluates the treatment areas for any localized reaction and discusses any reported symptoms. 3D facial digital images (frontal and profile images) are captured for objective calculation of the angle of chin retrusion. If the doctor determines at top-up follow-up visit that optimal (full) increase in chin projection or aesthetic contouring was not achieved after the initial treatment, then subject is advised that he may receive a top-up treatment.

A single repeat treatment is administered at a scheduled visit between months 18 and 24 if repeat treatment is warranted in the doctor's opinion and/or is desired by the subject. Injection volume for the chin does not exceed a total volume of 4.0 mL for the repeat treatment.

Although the invention has been described and illustrated with a certain degree of particularity, it is understood that the present disclosure has been made only by way of example, and that numerous changes in the combination and arrangement of parts can be resorted to by those skilled in the art without departing from the scope of the invention, as hereinafter claimed.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A composition comprising a crosslinked hyaluronic acid crosslinked with 1,4-butanediol diglycidyl ether;
   wherein the hyaluronic acid used for crosslinking comprises a mixture of:
   (i) at least 50% by weight, based on the total weight of the hyaluronic acid, of a low molecular weight hyaluronic acid having a weight average molecular weight of between about 750,000 Da and about 1.0 MDa, and
   (ii) a high molecular weight hyaluronic acid having a weight average molecular weight of between about 2.0 MDa and about 4.0 MDa; and
   wherein the composition:
   (a) has a hyaluronic acid concentration greater than 20 mg/g to about 30 mg/g,
   (b) has an elastic modulus between about 500 Pa and about 900 Pa at 5 Hz,
   (c) has a cohesivity between about 60 gmf and about 200 gmf,
   (d) has an extrusion force between about 4N and about 15N at 13 mm/min using a 1 mL COC syringe and a 27G×13 mm needle, and
   (e) is implantable subdermally or supraperiostially into the chin area, jawline, or nose of a patient.

2. The composition of claim 1, wherein the low molecular weight hyaluronic acid has a weight average molecular weight of between about 750,000 Da and about 0.99 MDa.

3. The composition of claim 1, wherein the high molecular weight hyaluronic acid has a weight average molecular weight of between about 2.4 MDa and about 3.6 MDa.

4. The composition of claim 1, wherein the hyaluronic acid concentration is about 22 mg/g to about 28 mg/g.

5. The composition of claim 1, wherein the hyaluronic acid concentration is about 24 mg/g to about 26 mg/g.

6. The composition of claim 1, wherein the hyaluronic acid concentration is about 25 mg/g.

7. The composition of claim 1, wherein the crosslinked hyaluronic acid has a degree of crosslinking of between about 4% and about 10%.

8. The composition of claim 1, wherein the hyaluronic acid used for crosslinking comprises a mixture of: (i) at least 70% by weight of the low molecular weight hyaluronic acid, and (ii) the high molecular weight hyaluronic acid.

9. The composition of claim 1, wherein the hyaluronic acid used for crosslinking comprises a mixture of (i) about 90% by weight of low molecular weight hyaluronic acid, based on the total weight of the hyaluronic acid, and (ii) about 10% by weight of the high molecular weight hyaluronic acid, based on the total weight of the hyaluronic acid.

10. The composition of claim 1, wherein the cohesivity is between about 60 gmf and about 100 gmf.

11. The composition of claim 1, wherein the extrusion force is between about 7N and about 12N at 13 mm/min using a 1 mL COC syringe and a 27G×13 mm needle.

12. The composition of claim 1, wherein the composition further comprises an anesthetic agent.

13. The composition of claim 12, wherein the anesthetic agent is lidocaine hydrochloride.

14. The composition of claim 1, wherein the composition further comprises uncrosslinked hyaluronic acid.

15. A composition, implantable subdermally or supraperiostially into the chin area, jawline, or nose of a patient, the composition comprising a crosslinked hyaluronic acid crosslinked with 1,4-butanediol diglycidyl ether;
wherein the crosslinked hyaluronic acid has a degree of crosslinking of between about 4% and about 10%;
wherein the hyaluronic acid used for crosslinking comprises a mixture of:
(i) at least 70% by weight, based on the total weight of the hyaluronic acid, of a low molecular weight hyaluronic acid having a weight average molecular weight of between about 750,000 Da and about 0.99 MDa, and
(ii) a high molecular weight hyaluronic acid having a weight average molecular weight of between about 2.4 MDa and about 3.6 MDa; and
wherein the composition has:
(a) a hyaluronic acid concentration of about 22.5 mg/g to about 27.5 mg/g,
(b) an elastic modulus between about 500 Pa and about 900 Pa at 5 Hz,
(b) a cohesivity between about 60 gmf and about 200 gmf, and
(e) an extrusion force between about 4N and about 12N at 13 mm/min using a 1 mL COC syringe and a 27G×13 mm needle.

16. A method of augmenting, correcting, restoring, or creating volume in a chin of a subject in need thereof, the method comprising injecting the composition of claim 15 into the chin of the subject.

17. A method of augmenting, correcting, restoring, or creating volume in the jawline or nose of a subject in need thereof, the method comprising injecting the composition of claim 15 into the jawline or nose of the subject.

18. A method of augmenting, correcting, restoring, or creating volume in a chin of a subject in need thereof, the method comprising injecting the composition of claim 1 into the chin of the subject.

19. A method of augmenting, correcting, restoring, or creating volume in the jawline of a subject in need thereof, the method comprising injecting the composition of claim 1 into the jawline of the subject.

20. A method of augmenting, correcting, restoring, or creating volume in nose of a subject in need thereof, the method comprising injecting the composition of claim 1 into the nose of the subject.

* * * * *